US010456201B1

(12) United States Patent
Solar et al.

(10) Patent No.: US 10,456,201 B1
(45) Date of Patent: Oct. 29, 2019

(54) SKULL-MOUNTED INSTRUMENT TRAJECTORY GUIDE

(71) Applicant: C2C Development, LLC, Melbourne, FL (US)

(72) Inventors: Matthew S. Solar, Indialantic, FL (US); Craig J. Pagan, West Melbourne, FL (US); Glenn D. Perry, Melbourne, FL (US)

(73) Assignee: C2C Development, LLC, Melbourne, FL (US)

( * ) Notice: Subject to any disclaimer, the term of this patent is extended or adjusted under 35 U.S.C. 154(b) by 796 days.

(21) Appl. No.: 14/826,849

(22) Filed: Aug. 14, 2015

Related U.S. Application Data

(60) Provisional application No. 62/117,740, filed on Feb. 18, 2015, provisional application No. 62/037,173, filed on Aug. 14, 2014.

(51) Int. Cl.
*A61B 90/11* (2016.01)
*A61B 19/00* (2006.01)

(52) U.S. Cl.
CPC ............ *A61B 19/201* (2013.01); *A61B 19/20* (2013.01)

(58) Field of Classification Search
CPC ... A61B 17/00234; A61B 19/20; A61B 19/22; A61B 19/201; A61B 19/5244; A61B 2017/3407
See application file for complete search history.

(56) References Cited

U.S. PATENT DOCUMENTS

| | | | |
|---|---|---|---|
| 4,805,615 A | 2/1989 | Carol | |
| 4,809,694 A | 3/1989 | Ferrara | |
| 5,201,742 A * | 4/1993 | Hasson | A61B 17/3403 606/1 |
| 5,601,569 A | 2/1997 | Pisharodi | |
| 6,018,094 A | 1/2000 | Fox | |
| 6,520,969 B2 | 2/2003 | Lambrecht et al. | |
| 6,529,765 B1 | 3/2003 | Franck et al. | |
| 6,902,569 B2 | 6/2005 | Parmer et al. | |
| 7,004,948 B1 | 2/2006 | Pianca et al. | |

(Continued)

FOREIGN PATENT DOCUMENTS

DE 10029368 A1 12/2001
EP 2324790 A1 5/2011

(Continued)

OTHER PUBLICATIONS

"U.S. Appl. No. 13/707,110, Examiner Interview Summary dated Nov. 12, 2013", 3 pgs.

(Continued)

*Primary Examiner* — Julie A Szpira
(74) *Attorney, Agent, or Firm* — Schwegman Lundberg & Woessner, P.A.

(57) ABSTRACT

An instrument guiding trajectory guide can include a ball-and-socket motion constrained by an arch. Z-height adjustment of a trajectory guide lumen can be provided, with or without a ball-and-socket, such as to permit target-centered alignment of the trajectory to a target. A polar-offset or x-y stage can be included. Contrast-enhanced imageable fiducial marker concentric rings can be used to help align the trajectory to the target. The concentric rings can be progressively smaller in a direction along the trajectory.

19 Claims, 29 Drawing Sheets

(56) References Cited

U.S. PATENT DOCUMENTS

| | | | |
|---|---|---|---|
| 7,204,840 B2 | 4/2007 | Skakoon et al. | |
| 7,497,863 B2 | 3/2009 | Solar et al. | |
| 7,815,651 B2 | 10/2010 | Skakoon et al. | |
| 8,747,419 B2 | 6/2014 | Solar et al. | |
| 8,979,871 B2 * | 3/2015 | Tyc | A61B 18/22 606/130 |
| 9,232,977 B1 * | 1/2016 | Rehman | A61B 90/11 |
| 9,445,793 B2 | 9/2016 | Solar et al. | |
| 2001/0003156 A1 | 6/2001 | Gill | |
| 2002/0049451 A1 | 4/2002 | Parmer et al. | |
| 2002/0052610 A1 * | 5/2002 | Skakoon | A61B 34/20 606/129 |
| 2003/0055436 A1 * | 3/2003 | Daum | A61B 90/11 606/130 |
| 2003/0229338 A1 * | 12/2003 | Irion | A61B 90/50 606/1 |
| 2005/0182420 A1 | 8/2005 | Schulte et al. | |
| 2009/0171184 A1 * | 7/2009 | Jenkins | G01R 33/286 600/411 |
| 2013/0096570 A1 | 4/2013 | Solar et al. | |
| 2014/0288578 A1 | 9/2014 | Solar et al. | |
| 2017/0007349 A1 | 1/2017 | Solar et al. | |

FOREIGN PATENT DOCUMENTS

| | | |
|---|---|---|
| WO | WO-0178814 A1 | 10/2001 |
| WO | WO-2009047494 A1 | 4/2009 |
| WO | WO-2011156701 A2 | 12/2011 |

OTHER PUBLICATIONS

"U.S. Appl. No. 13/707,110, Non Final Office Action dated Apr. 24, 2013", 16 pgs.

"U.S. Appl. No. 13/707,110, Notice of Allowance dated Jan. 30, 2014", 12 pgs.

"U.S. Appl. No. 13/707,110, Preliminary Amendment filed Jun. 3, 2014", 9 pgs.

"U.S. Appl. No. 13/707,110, Response filed Oct. 24, 2013 to Non Final Office Action dated Apr. 24, 2013", 24 pgs.

"U.S. Appl. No. 14/293,168, Final Office Action dated Feb. 4, 2016", 19 pgs.

"U.S. Appl. No. 14/293,168, Non Final Office Action dated Oct. 9, 2015", 16 pgs.

"U.S. Appl. No. 14/293,168, Notice of Allowance dated May 18, 2016", 12 pgs.

"U.S. Appl. No. 14/293,168, Response filed Jan. 6, 2016 to Non Final Office Action dated Oct. 9, 2015", 17 pgs.

"U.S. Appl. No. 14/293,168, Response filed May 4, 2016 to Final Office Action dated Feb. 4, 2016", 13 pgs.

"Dedicated for minimally invasive stereotactic neurosurgery", [Online]. Retrieved from the Internet: <URL: http://www.elekta.com/healthcare-professionals/products/elekta-neuroscience/stereotactic-neurosurgery/leksell-stereotactic-system.html>, (Accessed Oct. 24, 2013), 1 pg.

"International Application Serial No. PCT/US2011/039963, International Preliminary Report on Patentability dated Dec. 20, 2012", 12 pgs.

"International Application Serial No. PCT/US2011/039963, International Search Report dated Mar. 13, 2012", 6 pgs.

"International Application Serial No. PCT/US2011/039963, Invitation to Pay Additional Fees and Where Applicable, Protest Fee dated Nov. 2, 2011", 7 pgs.

"International Application Serial No. PCT/US2011/039963, Written Opinion dated Mar. 13, 2012", 10 pgs.

"U.S. Appl. No. 15/269,675, Non Final Office Action dated May 13, 2019", 8 pgs.

* cited by examiner

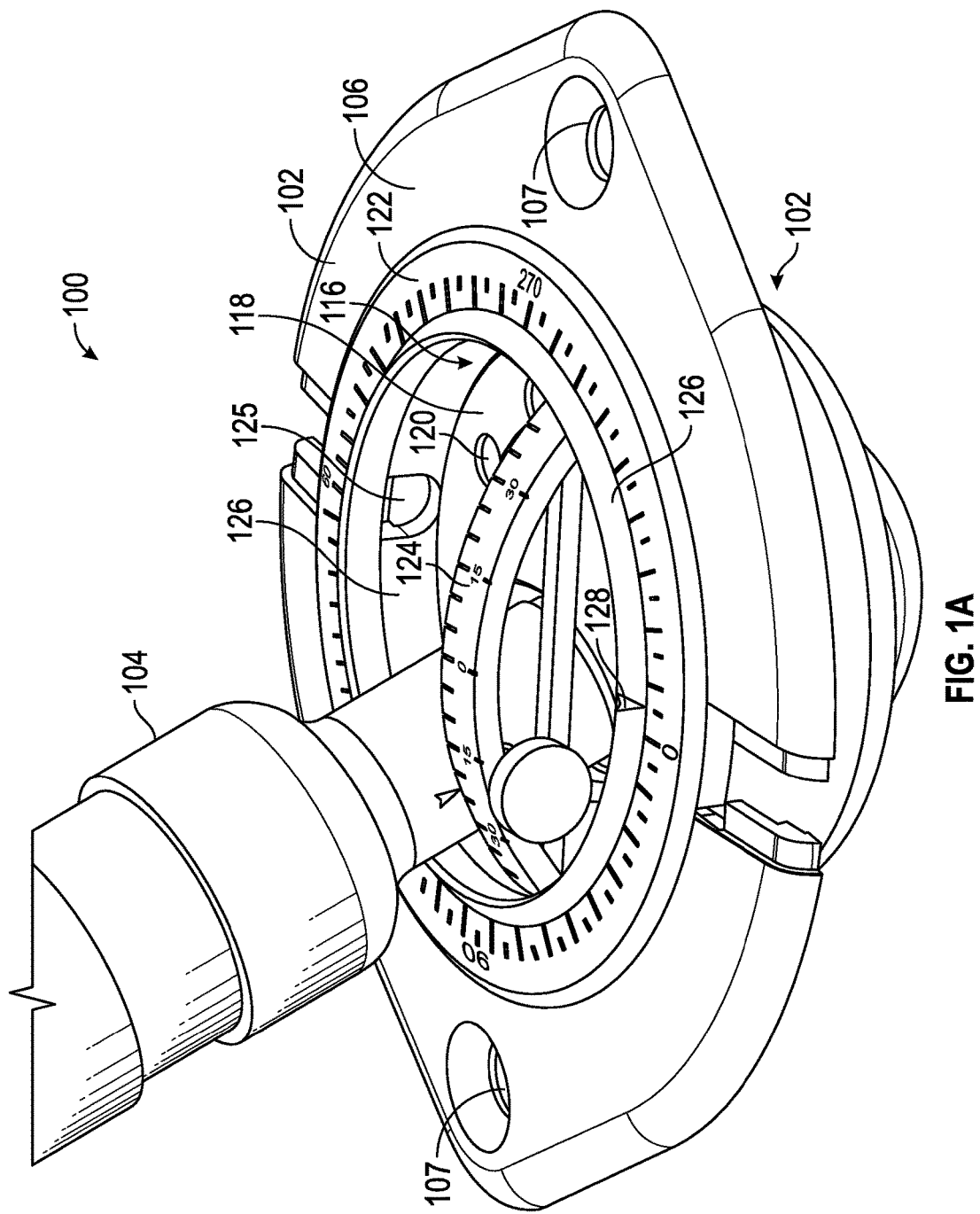

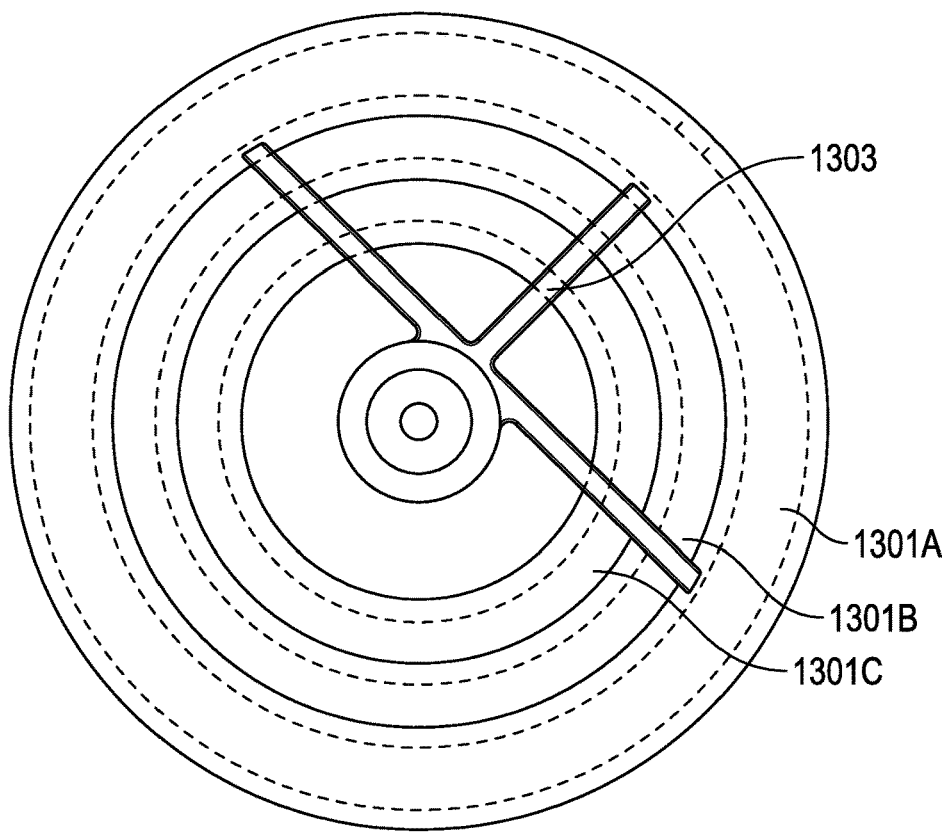
FIG. 13C
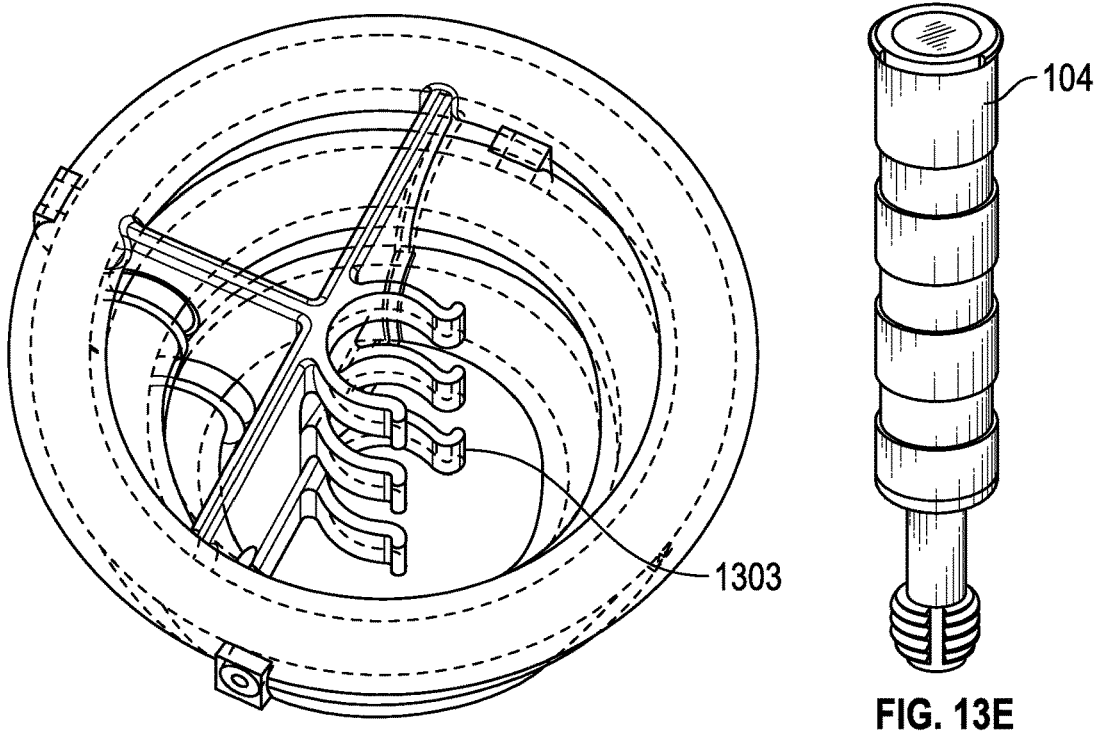
FIG. 13D
FIG. 13E

SKULL-MOUNTED INSTRUMENT TRAJECTORY GUIDE

CLAIM OF PRIORITY

This application claims the benefit of priority of U.S. Provisional Patent Application Ser. No. 62/037,173, filed Aug. 14, 2014, and U.S. Provisional Patent Application Ser. No. 62/117,740, each of which is incorporated by reference herein in its entirety.

BACKGROUND

A trajectory guide can be mounted onto a subject's skull about a desired skull entry portal, such as for guiding an instrument through the skull entry portal and toward a desired path into the subject's brain.

Carol U.S. Pat. No. 4,805,615 provides an example of a ball-and-socket trajectory guide.

Solar et al. U.S. Pat. No. 7,497,863 provides an example of a rotate-and-sweep trajectory guide.

Solar et al. U.S. Pat. No. 8,747,419 provides an example of a ball-and-socket trajectory guide in which a central pivot point of the ball is located below a surface of the skull when the base is affixed to the skull of a subject.

OVERVIEW

The present inventors have recognized, among other things, that a problem to be solved can include providing constrained rotate and tilt/sweep movement using a ball-and-socket trajectory guide, particularly in a low-profile manner, such as can allow a center pivot point of the ball to be located below a surface of the skull, such as within a burr hole or other entry portal. The present subject matter can help provide a solution to this problem, such as explained herein.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 13A, 13B, 13C, 13D, and 13E show an example of two or more concentric ring imageable fiducial marker rings, such as can be affixed to a proximal portion of the guide stem.

DETAILED DESCRIPTION

Figure 1B:
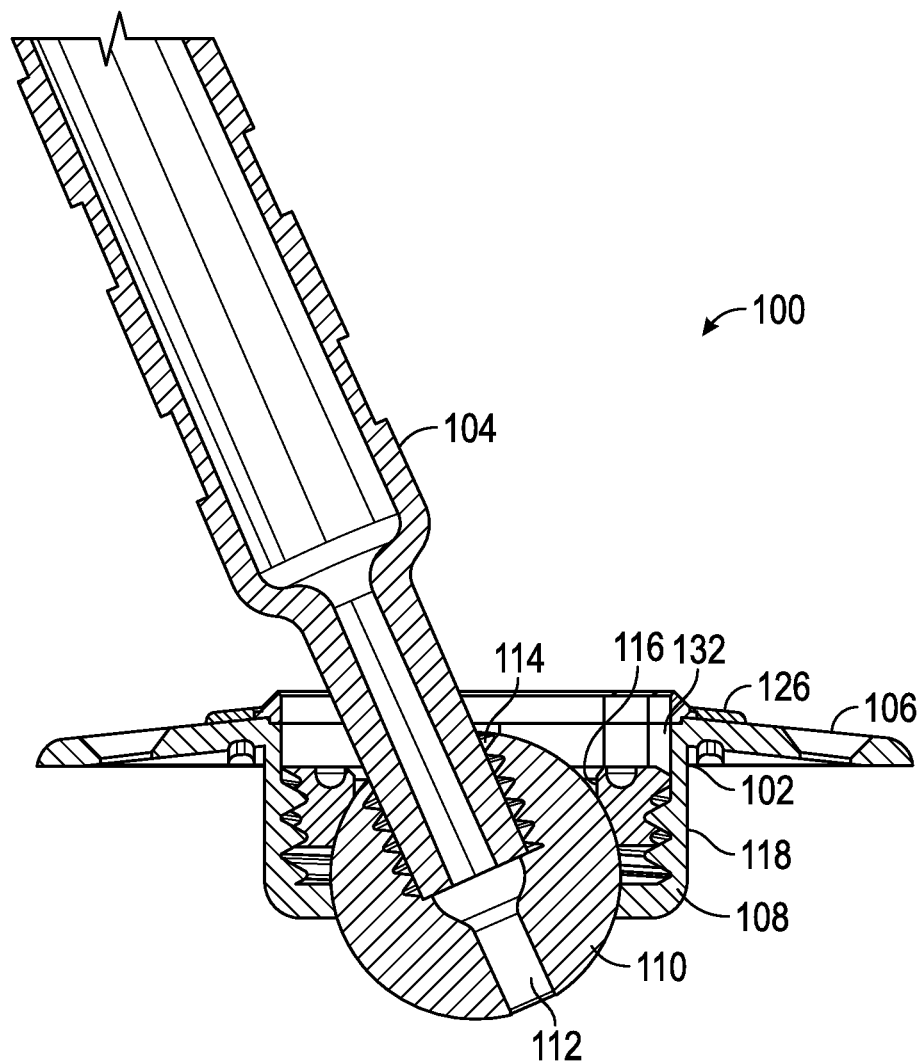
FIGS. 1A (plan view) and 1B (cross-section view) show an example of a skull-mounted trajectory guide that can be mounted onto a subject's skull about a desired skull entry portal, such as a burr hole, such as for guiding an instrument through the skull entry portal and toward a desired path into the subject's brain.
Figure 2:
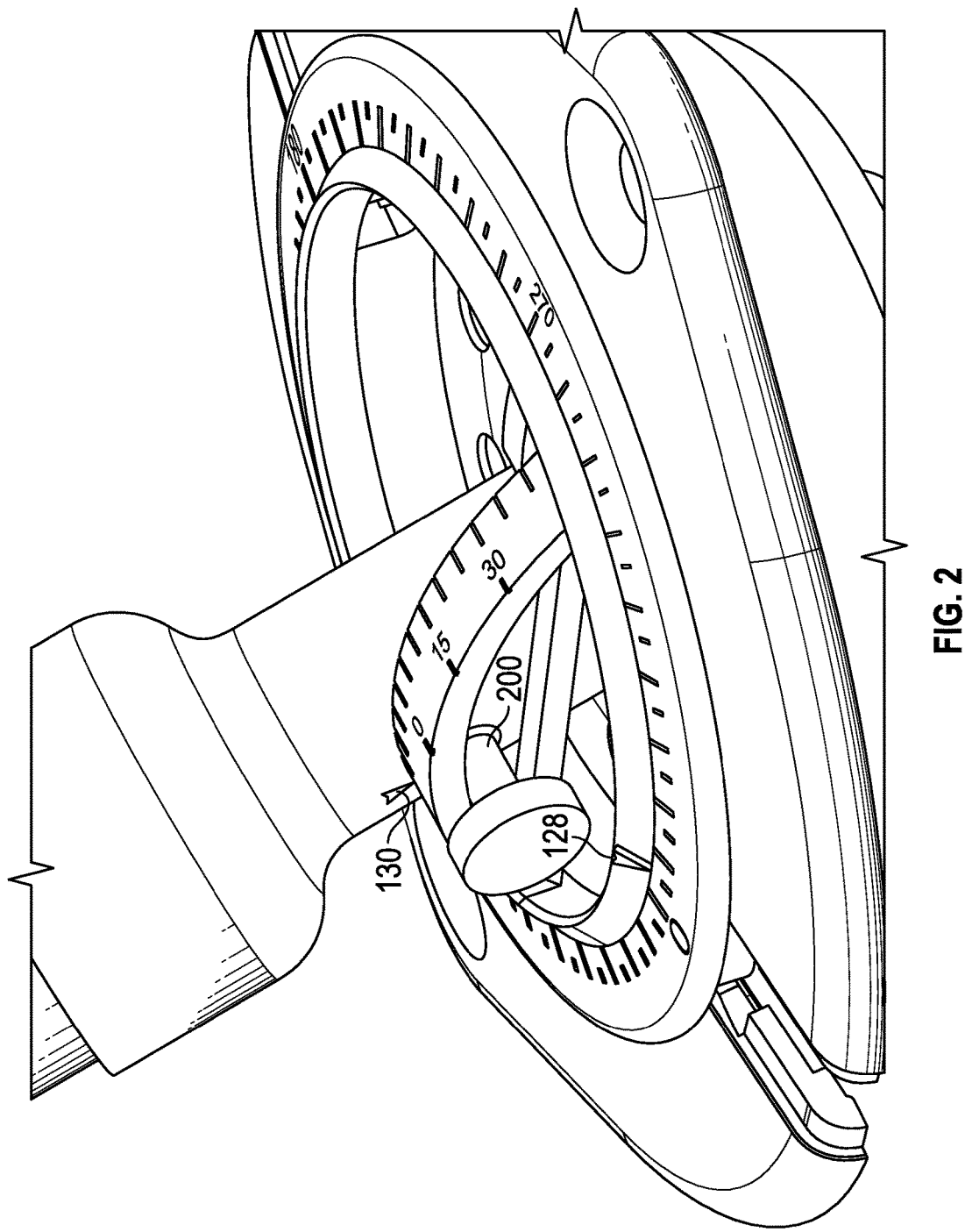
FIG. 2 shows a thumb screw or guide pin portion of a skull-mounted trajectory guide.

FIGS. 1A (plan view) and 1B (cross-section view) show an example of a body-mounted trajectory guide, such as a skull-mounted trajectory guide 100, that can be mounted onto a subject's skull such as about a desired skull entry portal, such as a burr hole, such as for guiding an instrument through the skull entry portal and toward a desired path into the subject's brain. The trajectory guide 100 can include a base 102 and an adjustably positionable instrument guide stem 104, which can be hollow or can include a lumen such as to allow passage of the guided instrument or other instrument therethrough. The base 102 can include a low-profile flange 106 that can extend laterally outward from a socket 108. The flange 106 can be secured to the subject's skull, such as via bone screws respectively extending through bone screw passages 107 on the flange 106. The socket 108 can be sized and shaped such that it can fit within the burr hole or other desired skull entry portal. The socket 108 can be sized and shaped to accept a spherical or other ball 110. The ball 110 can have a central pivot point within the socket 108 below a bottom surface of the flange 106, such as when the flange 106 is seated against the skull about the burr hole. The ball 110 can include a passage 112 therethrough. The passage 112 can be sized and shaped to permit the instrument being guided to pass therethrough. The passage 112 can include a proximal portion that can provide a receptacle 114 that can be sized and shaped to receive or engage a distal end of the guide stem 104, such as by threads or one or more other engagement features that can be respectively included within the passage or elsewhere on the ball 110 or on the distal portion of the guide stem 104.

The socket 108 can provide a proximally-facing internal receptacle 116, at least a portion of which can be sized and shaped to accept a spherical or other ball 110. The ball 110 can be pivotably seated against a bottom portion of the receptacle 116, such as with a central pivot point of the ball 110 being located below a bottom-facing surface of the flange 106. A portion of the ball 110 can protrude at least partially below the bottom portion of the receptacle 116, such as into the burr hole or other entry portal such as when the flange 106 is seated on the skull. A retainer ring 118 can be engaged into the receptacle 116 of the socket 108 such as to secure the ball 110 into a desired position such as to provide the desired trajectory for introducing the instrument through the guide stem 105, the entry portal, or to a desired location within the subject. The retainer ring 118 can include one or more threads or other engagement features such as to permit engagement of the retainer ring 118 into the socket 108, such as in a manner that can seat against a proximal portion of the ball 110 to secure the ball 110 in a desired pivoted position such as after the ball 110 has been pivotably adjusted by an end-user (or an automated or semi-automated control device) such as by manipulating the guide stem 104 to pivot the ball 110. The retainer ring 118 can also include one or more proximally-accessible engagement features 120, such as can be engaged from above by a tool or otherwise, such as to thread the retainer ring 118 into the receptacle 116 of the socket 108, such as to secure the ball 110.

The base 102 can also include a rotational alignment indicator, such as can be provided by one or more indicia or features on a rotational alignment ring 122. For example, the rotational alignment indicia can indicate degrees between 0 and 360 degrees about the circular rotational alignment ring 122. The rotational alignment ring 122 can be integrally formed with or fixed to the flange 106, or alternatively can be separately formed and rotatably engaged to the flange 106 such as to be rotated into a desired position, such as to align a desired rotational alignment indicator (e.g., 0 degrees) with a desired direction with respect to the subject (e.g., the anterior-posterior (A-P) direction or other desired direction), even if the base 102 is not aligned in any particular direction when mounted on to the subject's skull.

The base 102 can also include a pivot sweep guide arch 124, such as can extend proximally from a pivot sweep guide arch ring 126. The pivot sweep guide arch 124 can include a pivot sweep alignment indicator, such as can be provided by indicia or features on the pivot sweep guide arch 124 that can indicate a degree of tilt, such as in a forward or reverse direction from a vertical zero point. The pivot sweep guide arch ring 126 can include an arrow or other alignment indicator 128. The pivot sweep guide arch ring 126 can be rotated with respect to the rotational alignment ring 122, and the alignment indicator 128 can be read against the indicia on the rotational alignment ring 122, such as to provide an indication of rotational alignment.

The pivot sweep guide arch 124 can advantageously constrain movement of the ball 110 such that the guide stem 104 travels against the pivot sweep guide arch 124 when it is tilted by the end-user or a control device. In an example, such arching constraint of the guide stem 104 can be provided by a pin or thumbscrew 200 or other feature on the guide stem 104 that travels against the pivot sweep guide arch 124, such as along the underside of the pivot sweep guide arch 124, in such a manner that the guide stem 104 is constrained against the pivot sweep guide arch 124 during tilting. The thumbscrew 200 can be tightened, such as to secure the guide stem 104 at a desired forward or desired tilt, which can be read by an arrow or other alignment indicator against the indicia on the pivot sweep guide arch 124.

The thumbscrew 200 can alternatively be removed, and the desired tilt (and rotation) of the guide stem 104 can be secured such as by tightening the retainer ring 118 against the ball 110. For example, the location of the pivot sweep guide arch 124 can be laterally offset away from a center diameter of the pivot sweep guide arch ring 126, such as to allow space for a tool to be inserted within the pivot sweep guide arch ring 126, such as to engage one or more of the engagement features 120 on the retainer ring 118 such as to allow the retainer ring 118 to be secured against the ball 110.

A disc or other spacer 132 can optionally be located between the retainer ring 118 and the pivot sweep guide arch ring 126. The spacer 132 can include a center cutout such as to permit access to the engagement features 120 of the retainer ring 118 by a tool for tightening or loosening the retainer ring 118. The spacer 122 can also include one or more exit portals 125, such as can be sized and shaped and located to permit a leadwire, catheter, or other instrument to laterally exit the base 102, such as via the exit portals 125 or similar exit portals in the socket 108 or flange 106 portions of the base 102.

Figure 3:
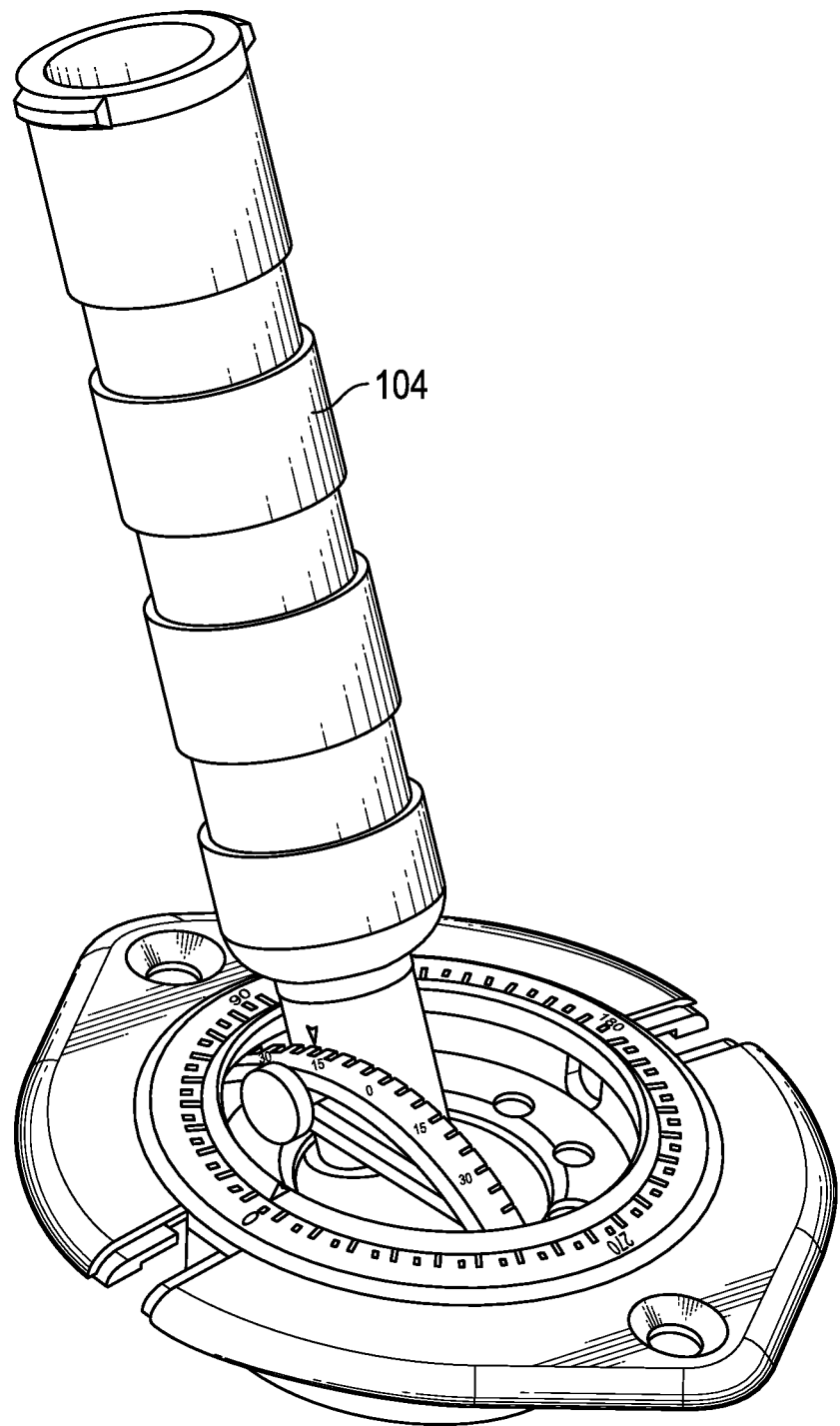
FIG. 3 shows another view of the trajectory guide with a proximal portion of the guide stem shown.
Figure 4A:
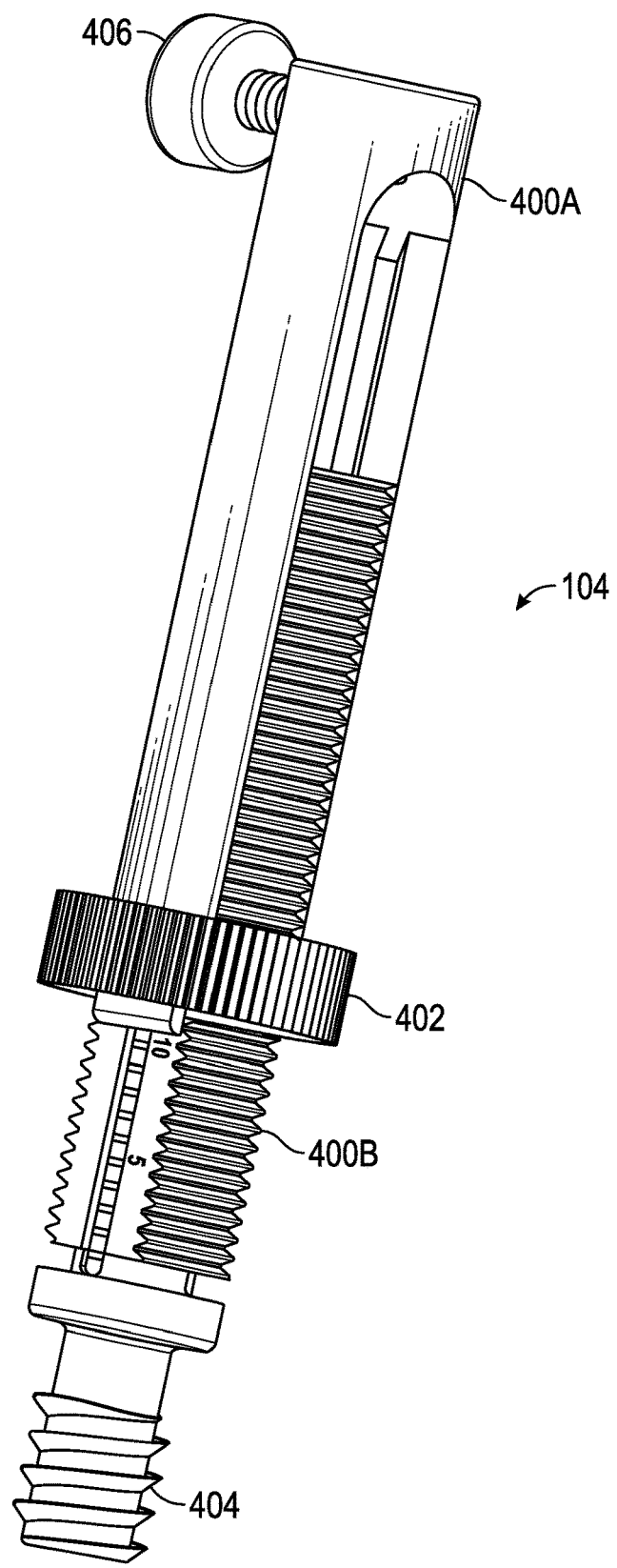
FIGS. 4A, 4B, 4C, 4D, 4E, 4F, 4G, 4H, and 4I show an example of a guide stem that can include a "Z-Direction" height adjustment.
Figure 4B:
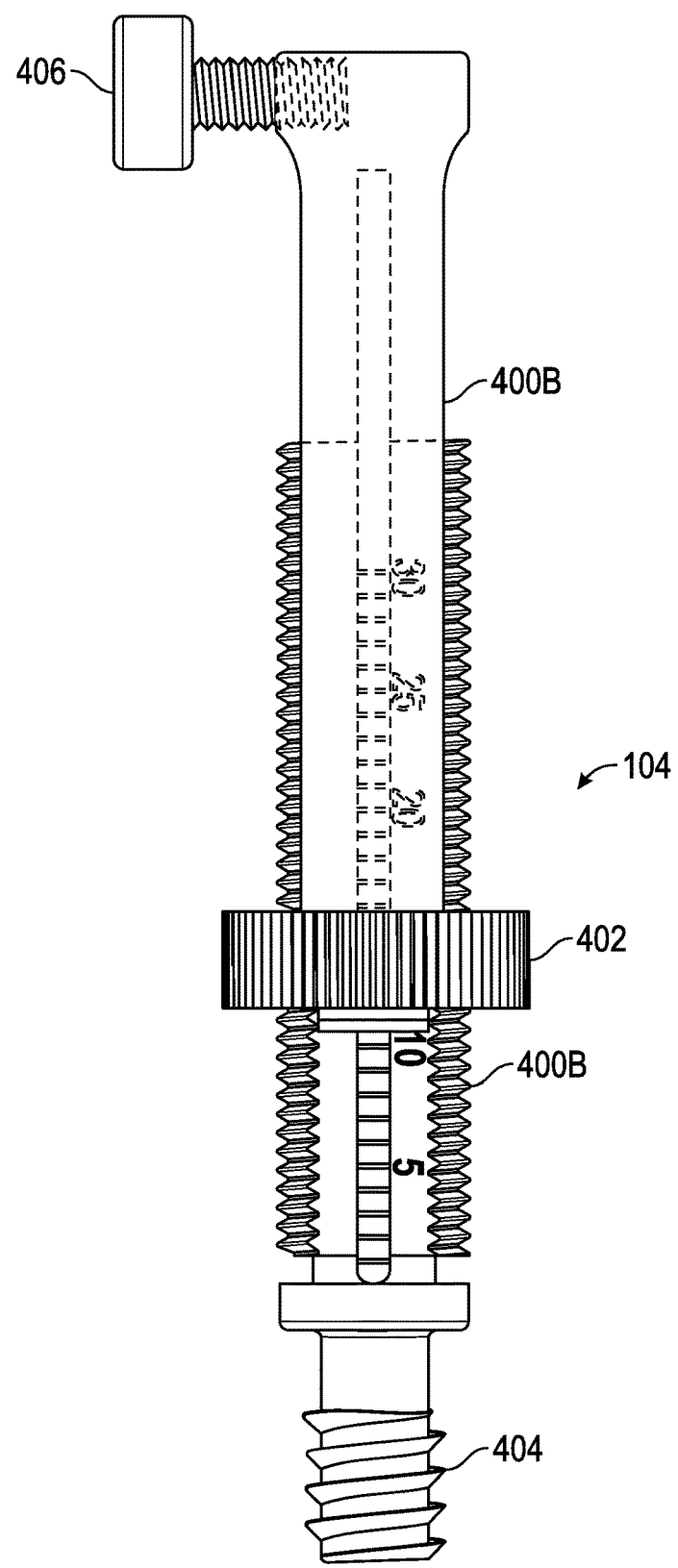
Figure 4C:
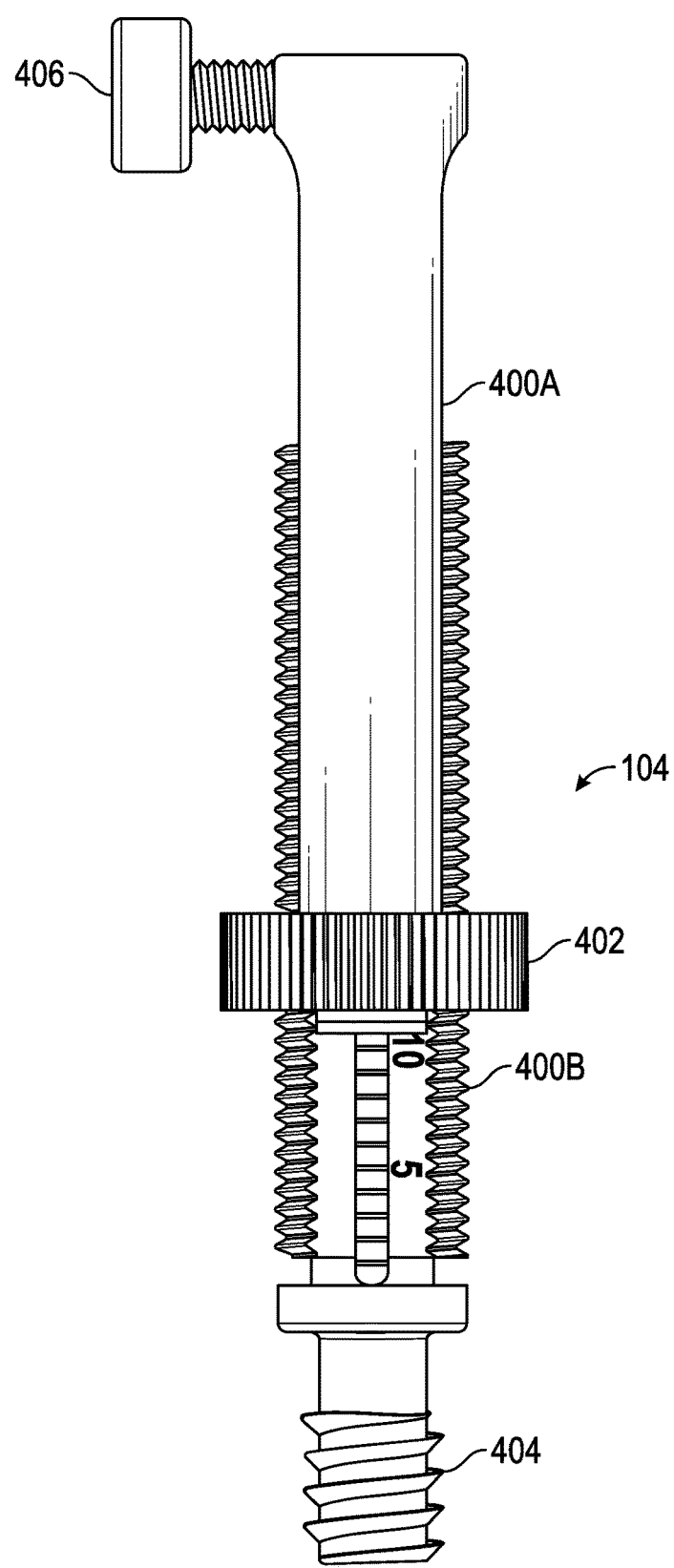
Figure 4D:
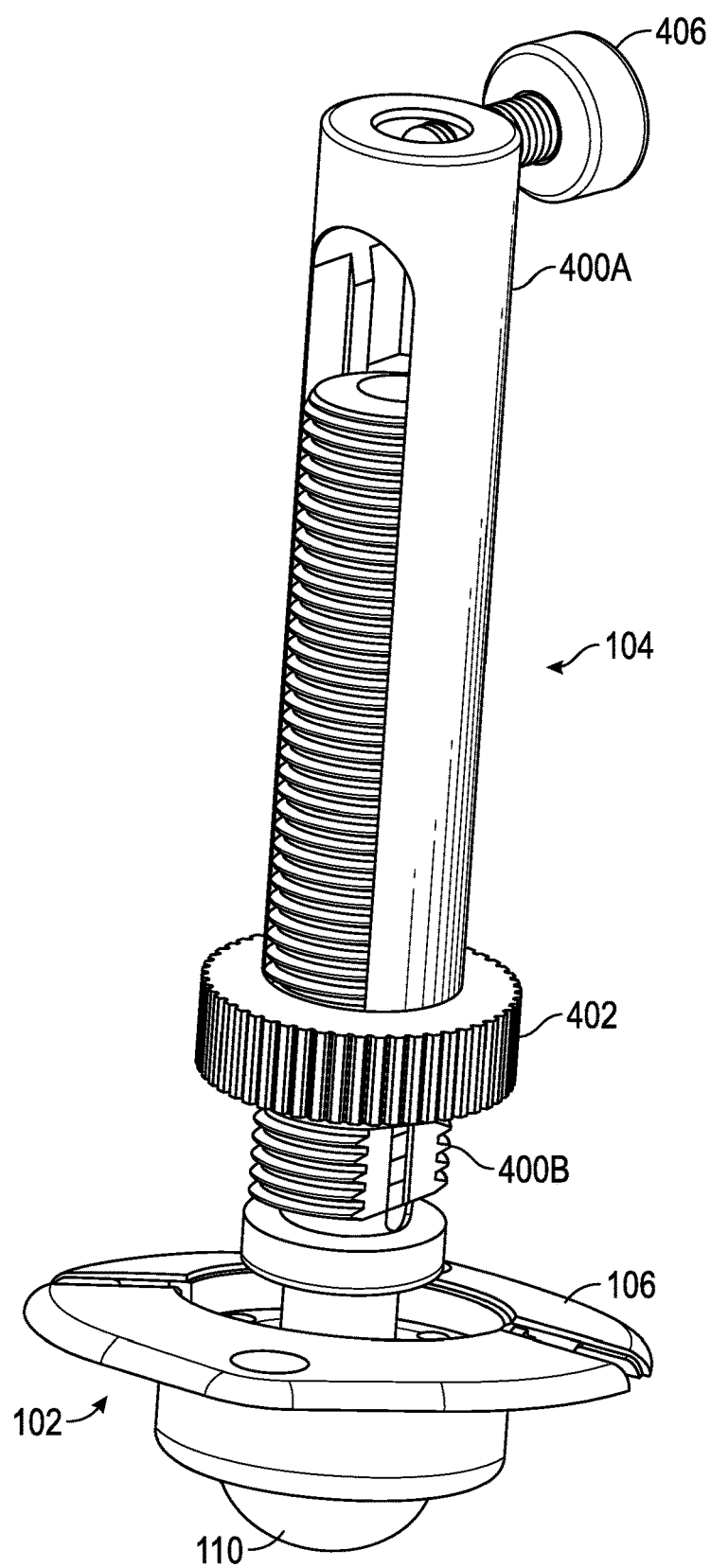
Figure 4E:
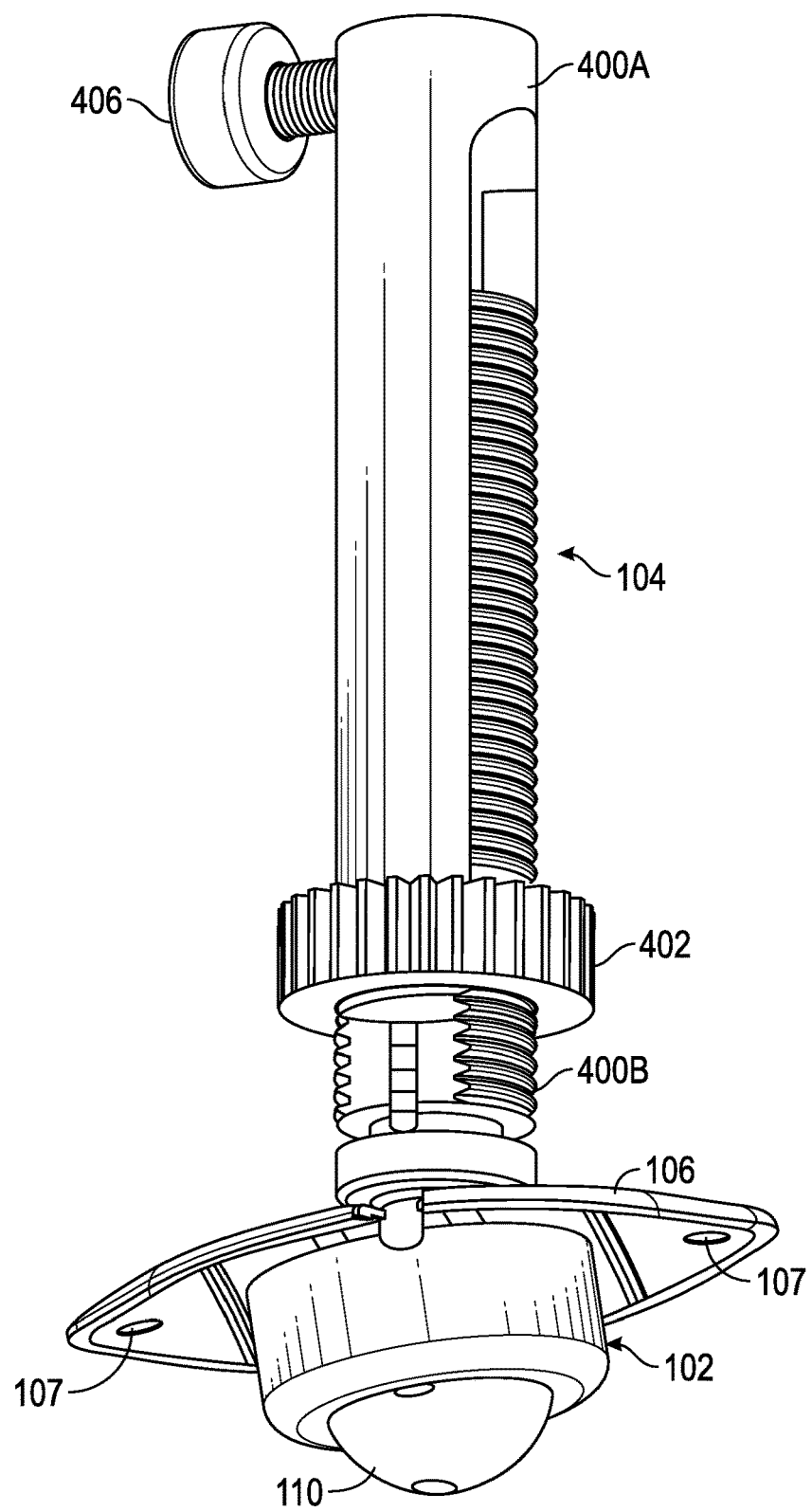
Figure 4F:
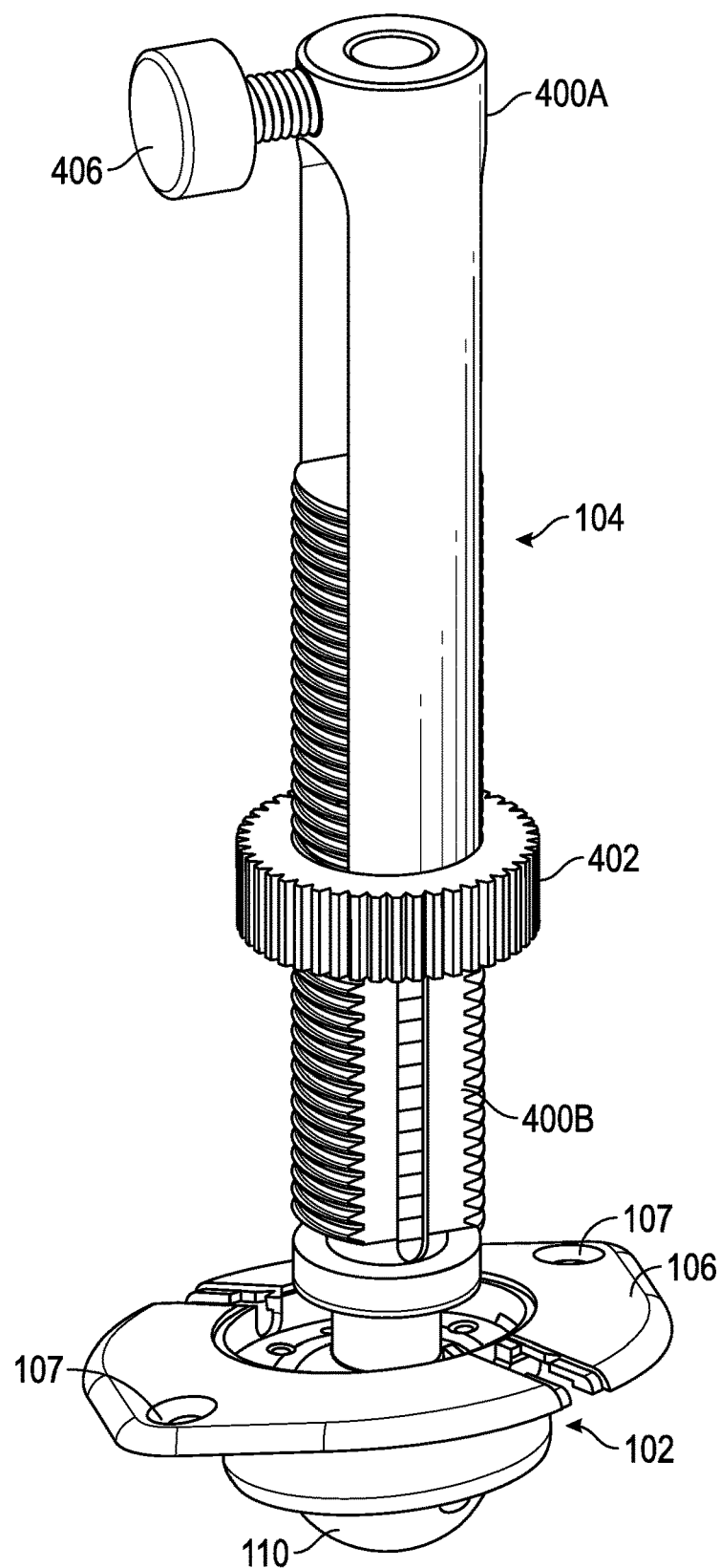
Figure 4G:
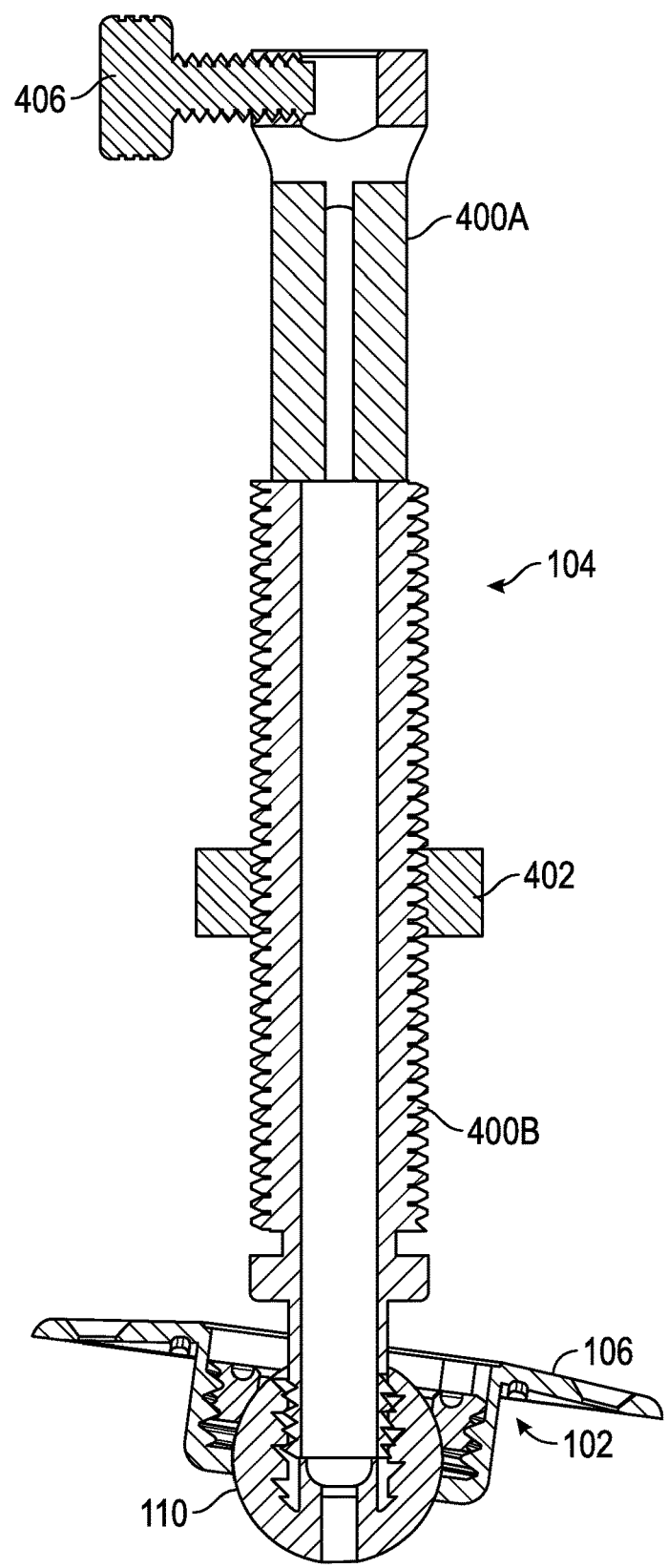
Figure 4H:
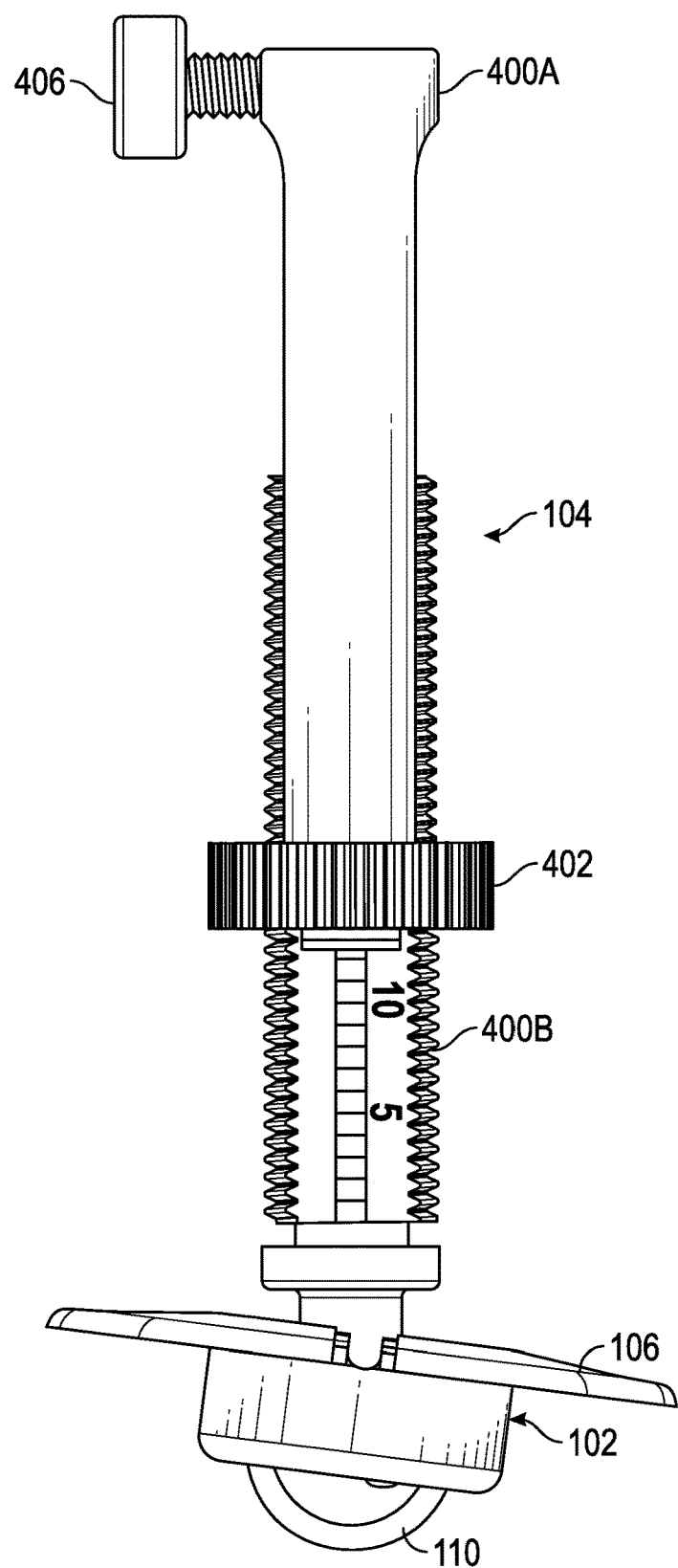
Figure 4I:
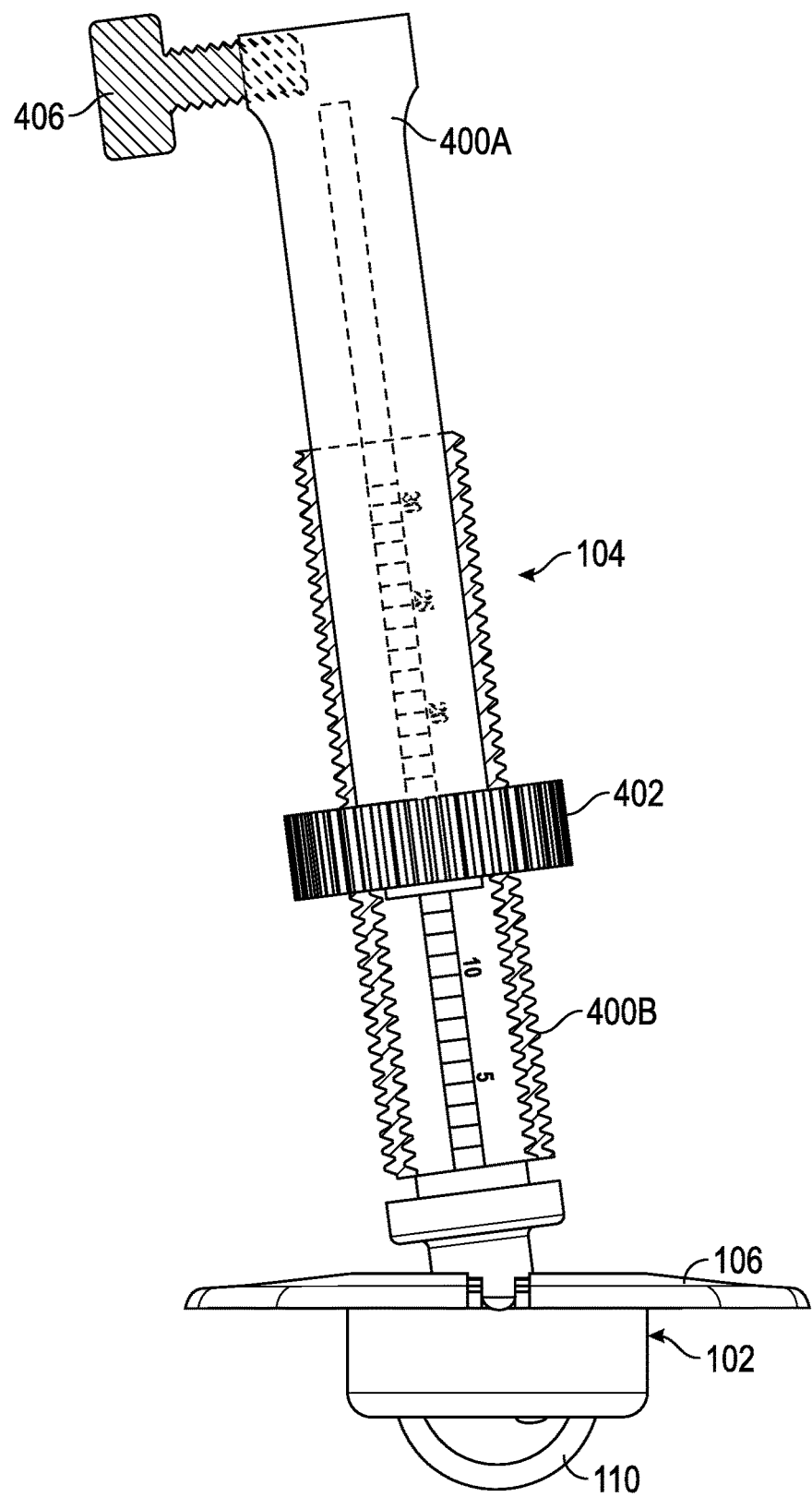
Figure 5A:
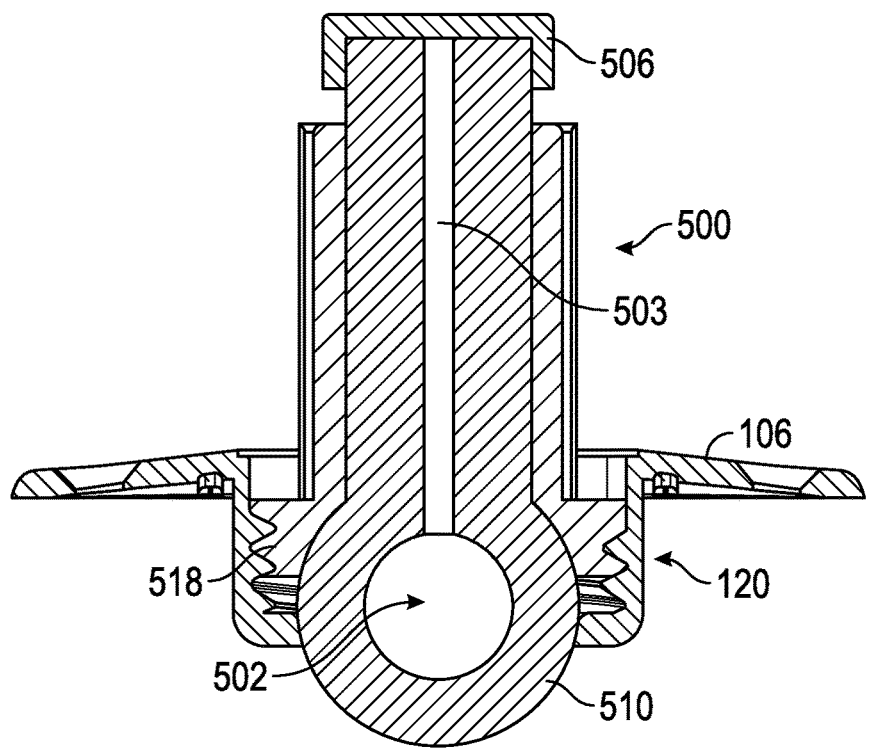
FIGS. 5A, 5B, 5C, 5D, and 5E show various views of an imaging fiducial stem that can be used together with the base.
Figure 5B:
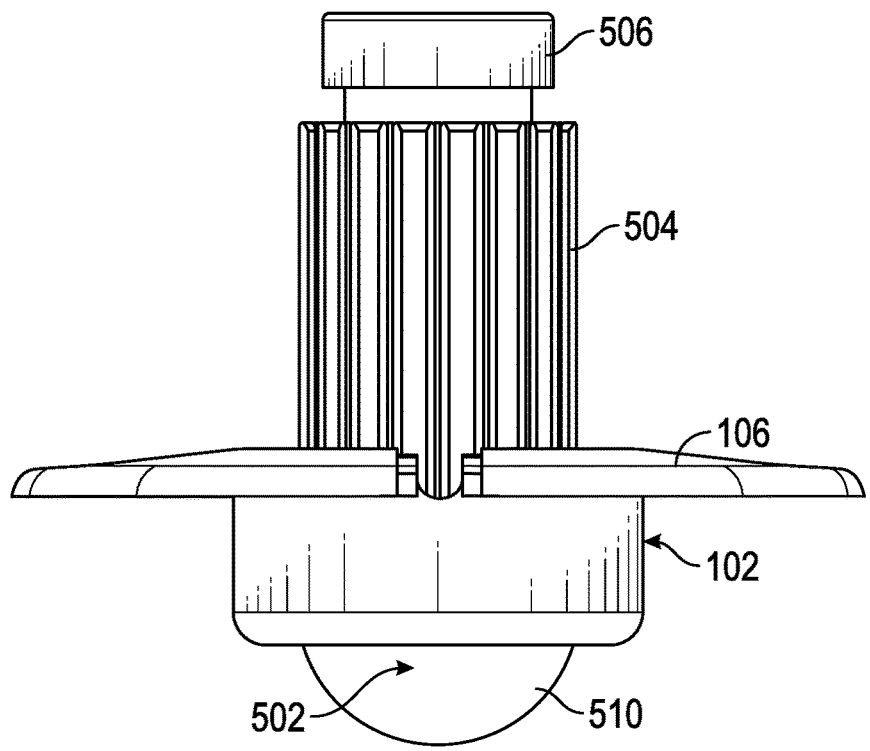
Figure 5C:
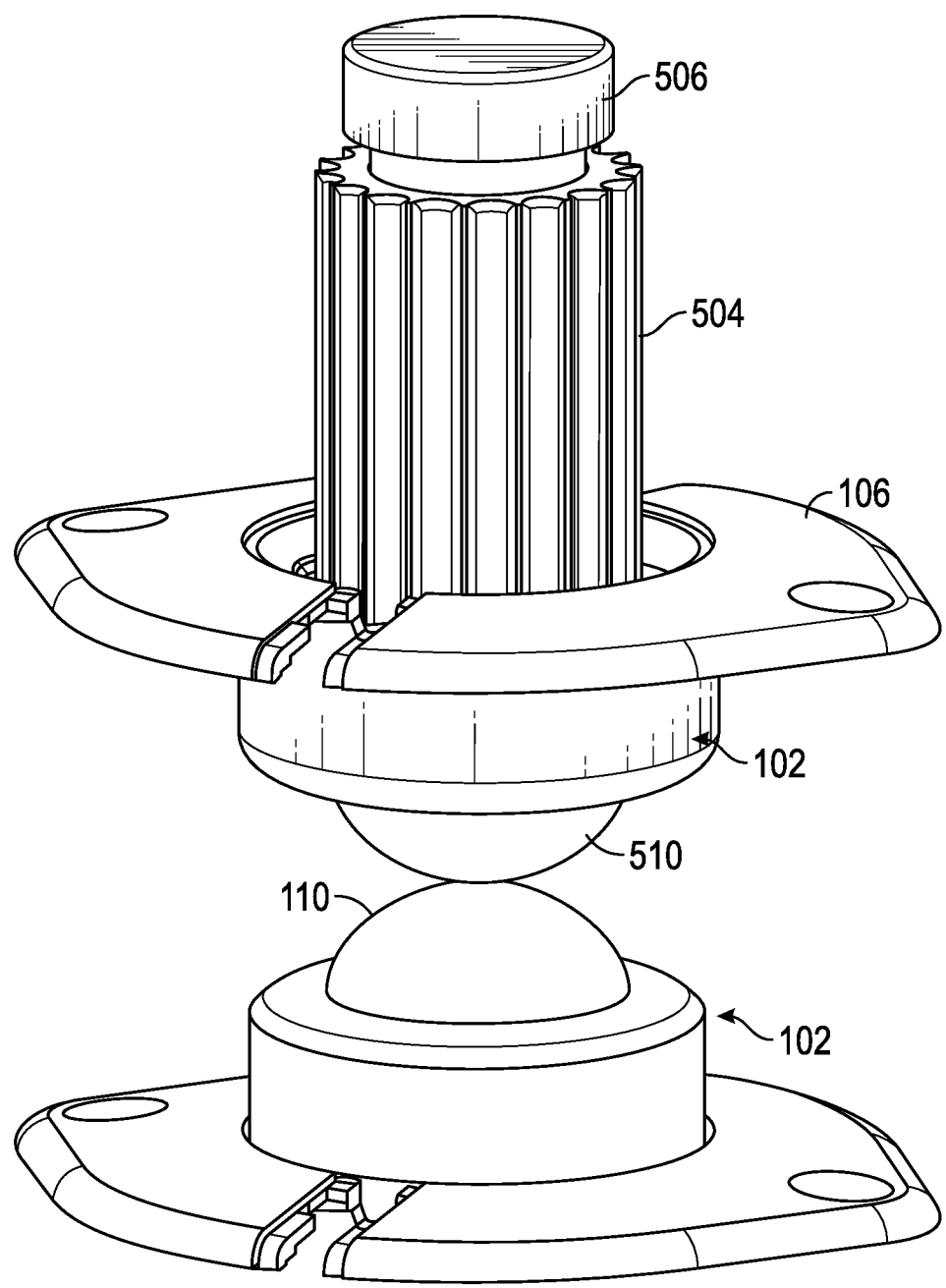
Figure 5D:
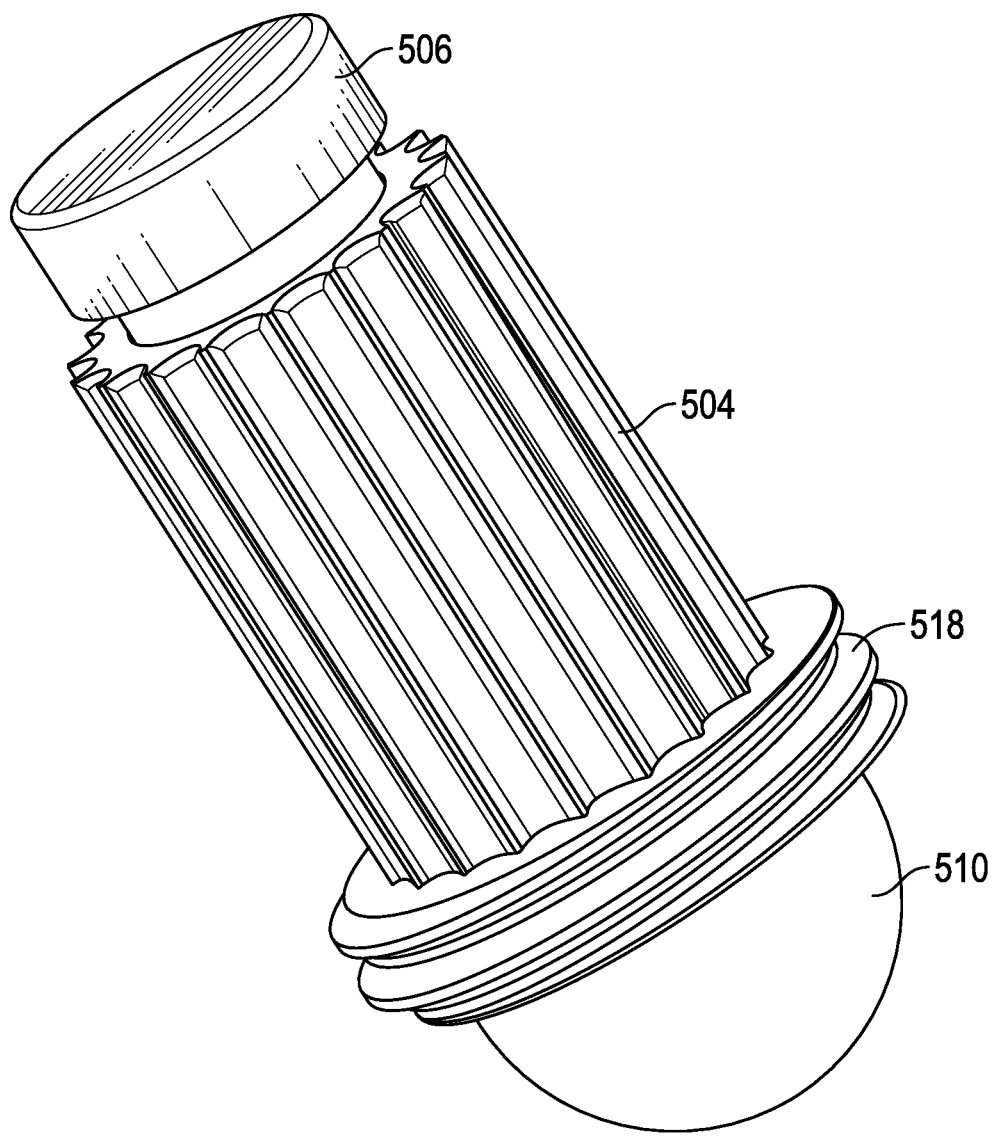
Figure 5E:
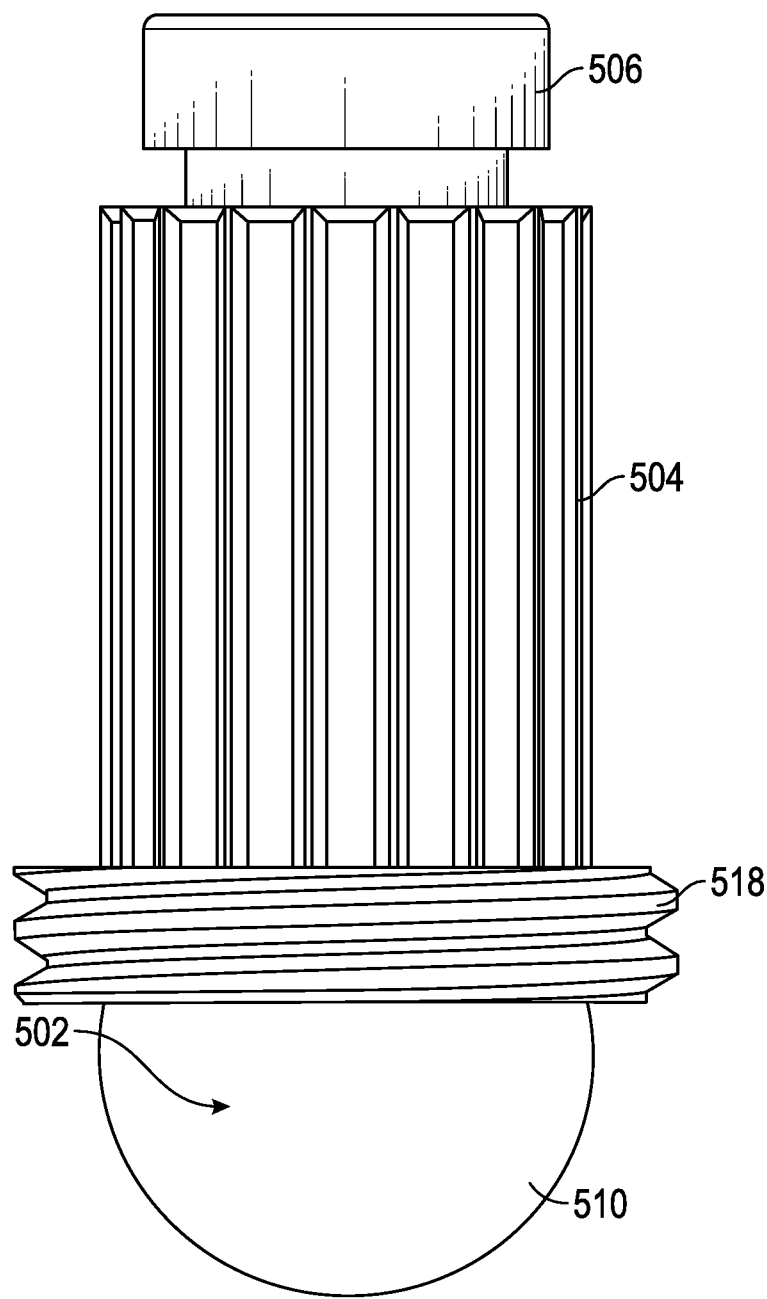
Figure 6A:
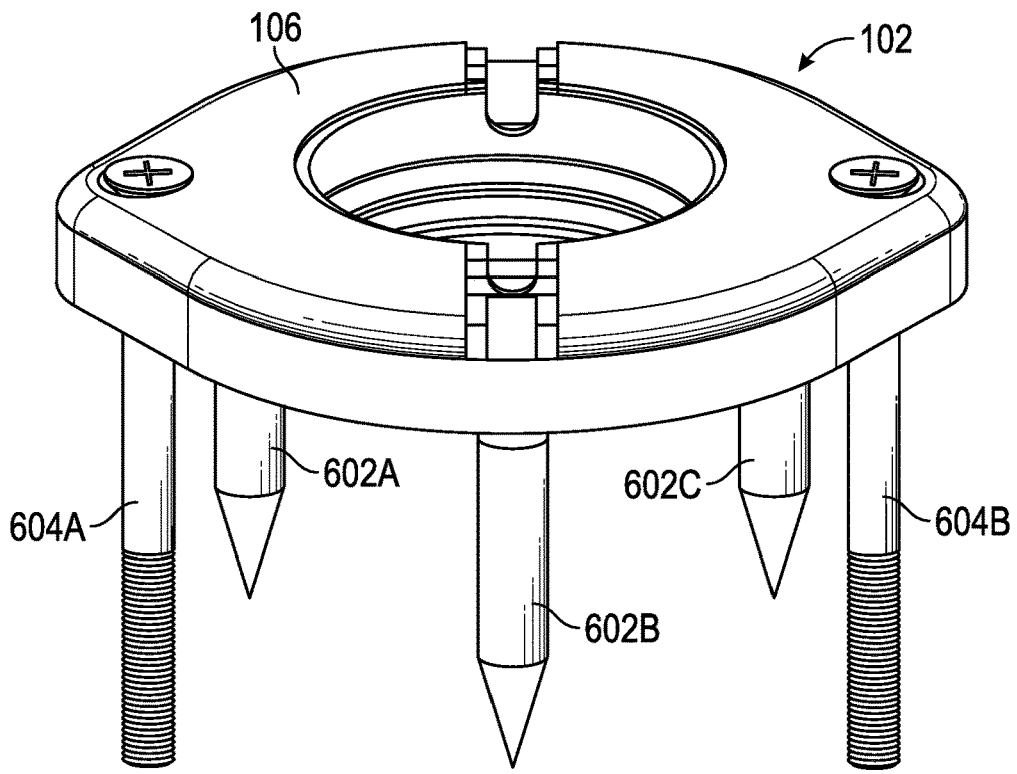
FIGS. 6A, 6B, 6C, and 6D show an example in which the base of the trajectory guide can optionally include three or more legs, such as to permit the base to be raised above the burr hole or other entry portal.
Figure 6B:
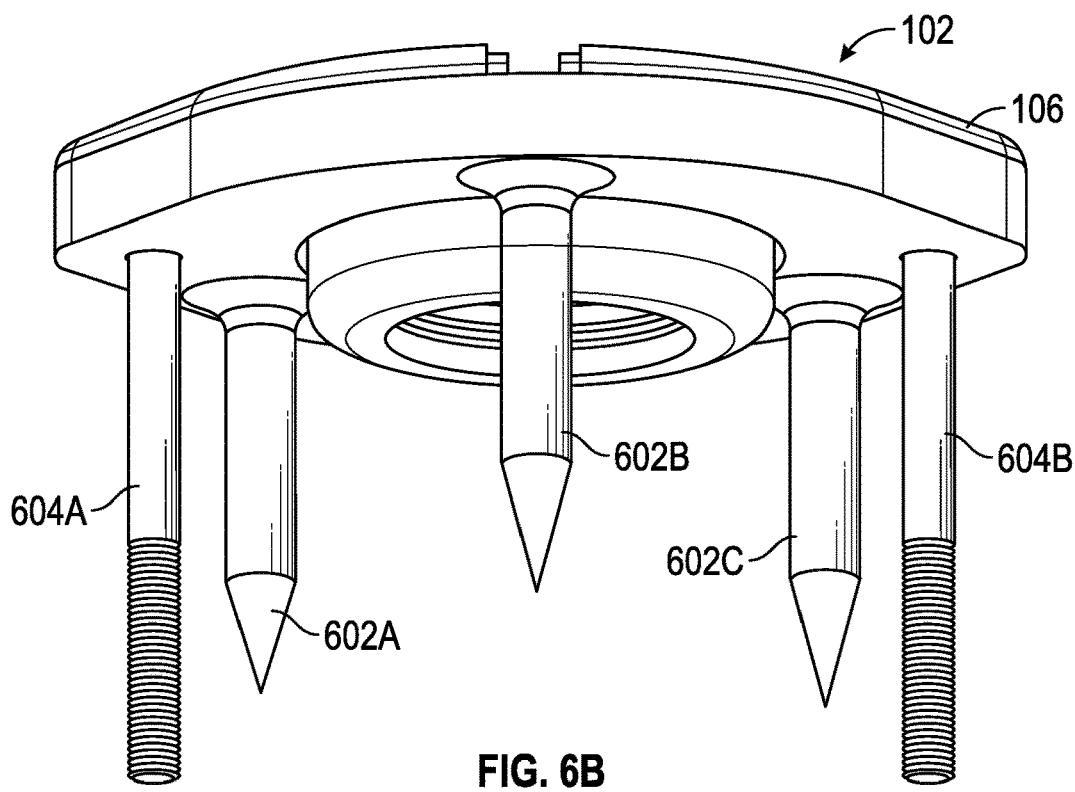
Figure 6C:
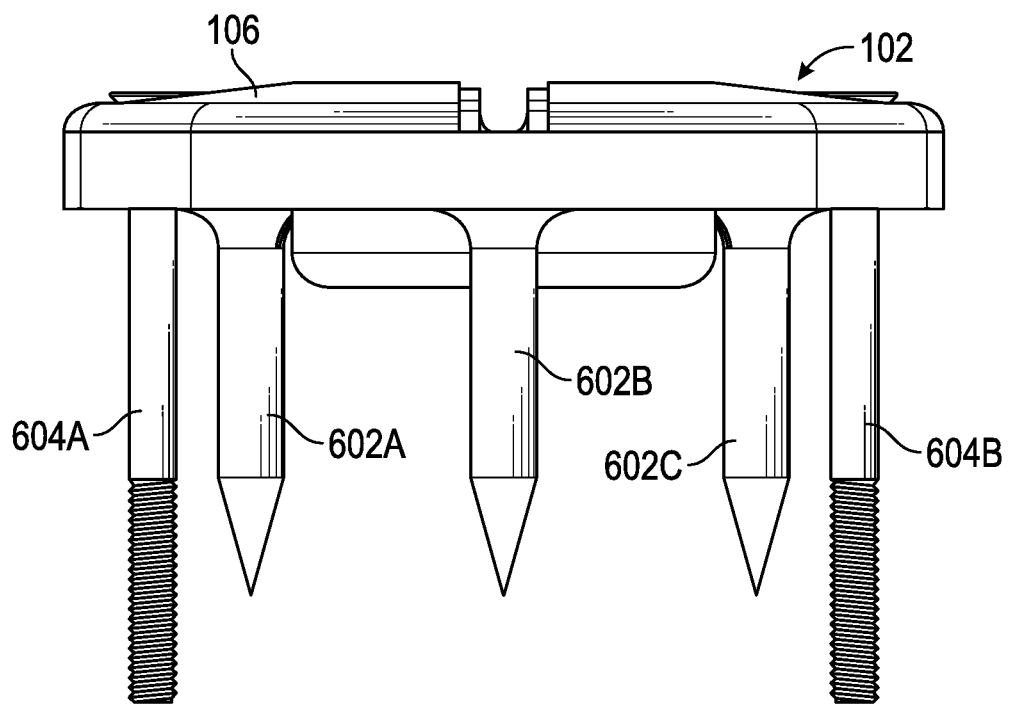
Figure 6D:
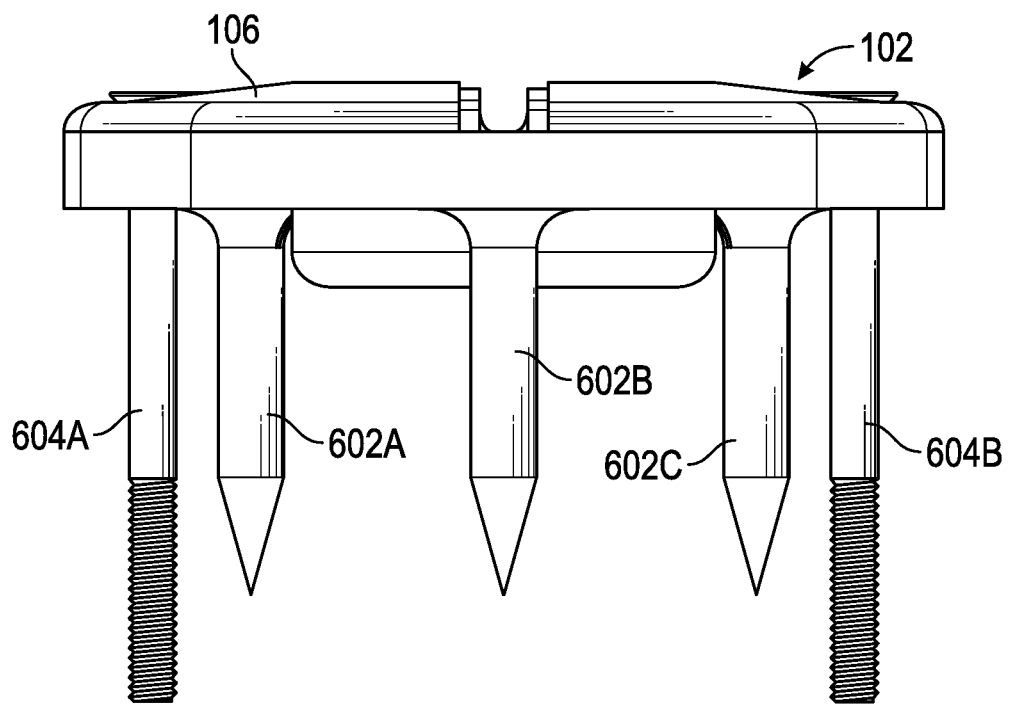

FIG. 3 shows another view of the trajectory guide 100 with a proximal portion of an example of the guide stem 104 shown.

FIGS. 4A, 4B, 4C, 4D, 4E, 4F, 4G, 4H, and 4I show an example of a guide stem 104 that can include a "Z-Direction" height adjustment, such as for providing a desired height or length of the guide stem 104 or for mounting one or more other components to the guide stem 104 at a desired Z-Direction height. For example, the guide stem 104 can include two components, such as an inner shaft or sleeve 400A and an outer sleeve 400B, such as can be threadably coupled with respect to each other, such as to provide a desired height of the guide stem 104. In an example, a threaded thumb wheel 402 can be engaged to one of the inner or outer sleeves 400A-B and turned by the user such as to threadably adjust the longitudinal position of the sleeves 400A-B with respect to each other. Height indicia can be provide on one of the inner or outer sleeves 400A-B and read against an end or other indicator on the other of the inner or outer sleeves 400A-B, such as to provide an indication of the then-current value of the Z-Direction height adjustment.

The guide stem 104 can include distal threads 404, such as for being threaded into the ball 110, such as explained above. The guide stem 104 can include a thumb screw 406, such as at a proximal end of the guide stem 104, such as to secure one or more components to the guide stem, such as before or after Z-height adjustment of the guide stem 104.

FIGS. 5A, 5B, 5C, 5D, and 5E show various views of an imaging fiducial stem 500 that can be used together with the base 102, such as instead of one or more of the guide stem 104, the ball 110, and the retainer ring 118, such as during an imaging session by a medical imaging modality, such as magnetic resonance imaging (MR or MRI), computed tomography (CT), or positron emission tomography (PET). The imaging fiducial stem 500 can include one or more imageable fiducial components that show up on the selected one or more imaging systems, such as with sufficient contrast to allow medical diagnosis or treatment. For example, the imaging fiducial stem 500 can include a fiducial marker that can clearly demarcate on an imaging display the central pivot point of the pivoting ball 110 of the trajectory guide 100. Optionally, one or more other aspects of the trajectory guide 100 (e.g., the ball 110, the base 102, the guide stem 104, etc.) can additionally or alternatively be demarcated on an imaging display, such as by one or more other contrast-enhanced or other fiducial markers. When an imaging scan has been created that marks the pivot point, the imaging fiducial stem 500 can be removed and the subject can either be (1) "stitched up" and sent home for further medical procedures on another day, or (2) sent on for further medical procedures on the same day.

For example, for MRI, the imaging fiducial stem 500 can include one or more of an imageable (e.g., fluid-filled with a MR contrast agent) ball central pivot location fiducial marker 502 and an optional imageable (e.g., fluid filled with a contrast agent) longitudinal instrument guide trajectory fiducial marker 503, both of which can be configured to provide good contrast on an MRI image, such as from the materials of the trajectory guide 100, the subject's skull and brain tissue, or both. The fiducial markers 502 and 503 can be formed from the same unitary chamber within the imaging fiducial stem 500, such as to accept a fluid contrast agent. A seal or cap 506 can be located at a fluid intake port to the chamber to seal and confine the fluid contrast agent within the imaging fiducial stem 500.

The imaging fiducial stem 500 can be sized and shaped and otherwise configured to mimic the alignment guide stem 104, such that when the imaging fiducial stem 500 is inserted in and fully threaded into the receptacle 116 of the socket 108, the center of the fiducial marker 502 is at the same location that the center of the ball 110 would be if the imaging fiducial stem 500 were replaced by the ball 110, the retainer 118, and the guide stem 104. Similarly, the fiducial marker 503 will be at the same location that the instrument-guiding trajectory provided by the center passage of the guide stem 104 would be if the imaging fiducial stem 500 were replaced by the ball 110, the retainer 118, and the guide stem 104.

In an example, the imaging fiducial stem 500 can include (such as in a single component) a ball portion 510 (e.g., mimicking ball 110), a threaded retainer 518 that can be integrally formed with or otherwise attached to the ball portion 510 (e.g., mimicking the retainer 118), and a guide stem 504 (e.g., mimicking the guide stem 104) that can be integrally formed with or otherwise attached to the threaded retainer 518 and the ball portion 510).

In this way, the imaging fiducial stem 500 can be used, such as during preoperative or intraoperative imaging session, to plan the trajectory of the instrument insertion under MR imaging guidance, and the guide stem 104, ball 110, and retainer 118 can be used later, such as to obtain the same desired alignment using the information from the imaging session.

FIGS. 6A, 6B, 6C, and 6D show an example in which the base 102 of the trajectory guide 100 can optionally include three or more legs 602, such as to permit the base 102 to be raised above the burr hole or other entry portal. The legs 602 can include sharp tips at their distal ends, away from the base 102, such as to help plant the legs 602 against the subject's skull and to inhibit or prevent sliding relative to the subject's skull. One or more bone screws 604 can be used to secure the raised base 102 to the subject's skull at the desired location. The one or more bone screws can be passed through one or more screw hole openings 107 in the flange 106 of the base 102. The raised base 102 such as shown in FIGS. 6A-6D can help provide an ability to align the trajectory first, and then drill (e.g., by extending a drill bit through the center lumen of the guide stem 104) an "on-trajectory" hole through the subject's skull to provide an entry portal. The resulting "on-trajectory" hole can be smaller than a typical (e.g., 14 millimeter) burr hole.

Figure 7:
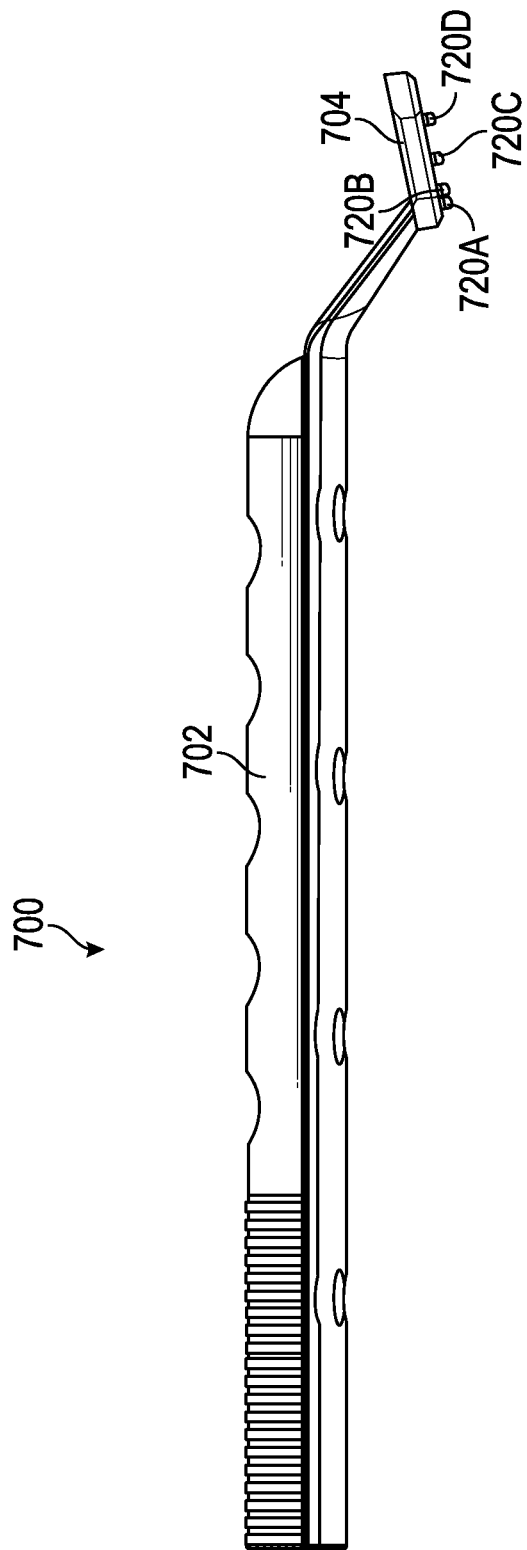
FIG. 7 shows an example of a wrench or other tool that can be used to tighten the retainer ring to secure the ball in a desired position.

FIG. 7 shows an example of a wrench or other tool 700 that can be used to tighten the retainer ring 118 to secure the ball 110 in a desired position, which, in turn, can provide the desired instrument trajectory via the guide stem 104 that can be attached to the ball 110. The tool 700 can include a handle 702 and a working distal portion 702 that can be sized, shaped, or otherwise configured to be placed flat against the retainer ring 118 with one or more engagement features 720 (such as protrusions) engaged with one or more corresponding engagement features 120 in the retainer ring 118. An outer circumference of the working distal portion 702 can be sized to fit within the receptacle 116 of the socket 108, such as to permit turning the working distal portion 702 to thread the retainer ring 118 into the receptacle 116 of the socket 108.

Figure 8:
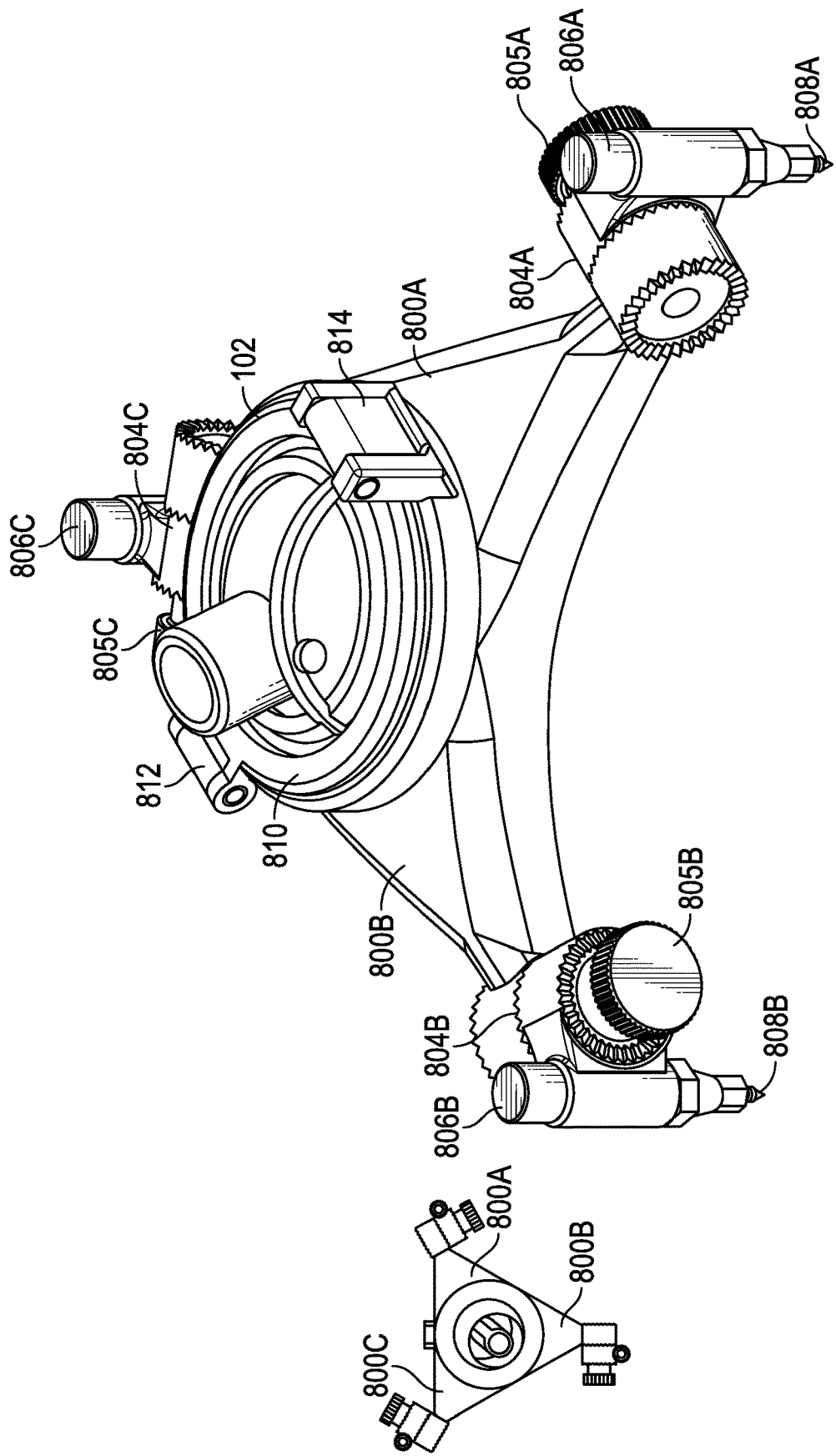
FIG. 8 shows an example of a skull mounted trajectory guide in which the base can be raised above the skull, e.g., along with the ball and the socket.

FIG. 8 shows an example in which the skull mounted trajectory guide 100 (e.g., such as shown in FIG. 1A, 1B, 2, or 3) in which the base 102 can be raised above the skull, along with the ball 110 and the socket 108. In an example, this can include providing a tripod, a single leg or other support, or a plurality of legs 800, such as can extend laterally outward or down toward the skull, or both. In FIG. 8, the legs 800A-C can include or be coupled to feet 802A-C, such as at the peripherally distal portions of the legs 800A-C. The feet 802A-C can be angularly or otherwise adjustable, such as by including a locking serrated joint 804A-C, such as a Hirth joint or Hirth coupling, such as can be locked using a thumbscrew to draw opposing serrated disks of the joint together. The feet 802A-C can include a fixed or height-adjustable peg 806A-C on a peripheral portion of the respective joint 804A-C. The pegs 806A-C can be height adjustable, such as by being threadable with a receptacle on the peripheral portion of the respective joint 804A-C, such as using thumbscrews 805A-C for the pegs 806A-C or using another height adjustment technique. The pegs 806A-C can include sharp threaded bone screw distal tips 808A-C, such as to secure the pegs 806A-C and, in turn, the entire base 102, to the skull.

The position of the rotating or swiveling ball 110 can be secured within the socket 108, such as by using a clamping retaining ring 810. The retaining ring 810 can be can be pressed downward such as to clamp over the ball 110. A hinge 812 can couple the retaining ring 810 to the base 102. A user-engageable and user-disenageable clasp 814 can secure the retaining ring 810 to the base 102. In an example, the raised base 102 or the raised socket 108, or both, can include a light-emitting diode (LED) or other lamp, such as on the underside toward the skull, such as to provide light that can be directed toward the burr hole or other desired location of the skull underneath the raised base 102 or the raised socket 108. A local or remote power supply can be provided such as to provide electrical power to the lamp such as via a wired connection to the lamp.

Figure 9:
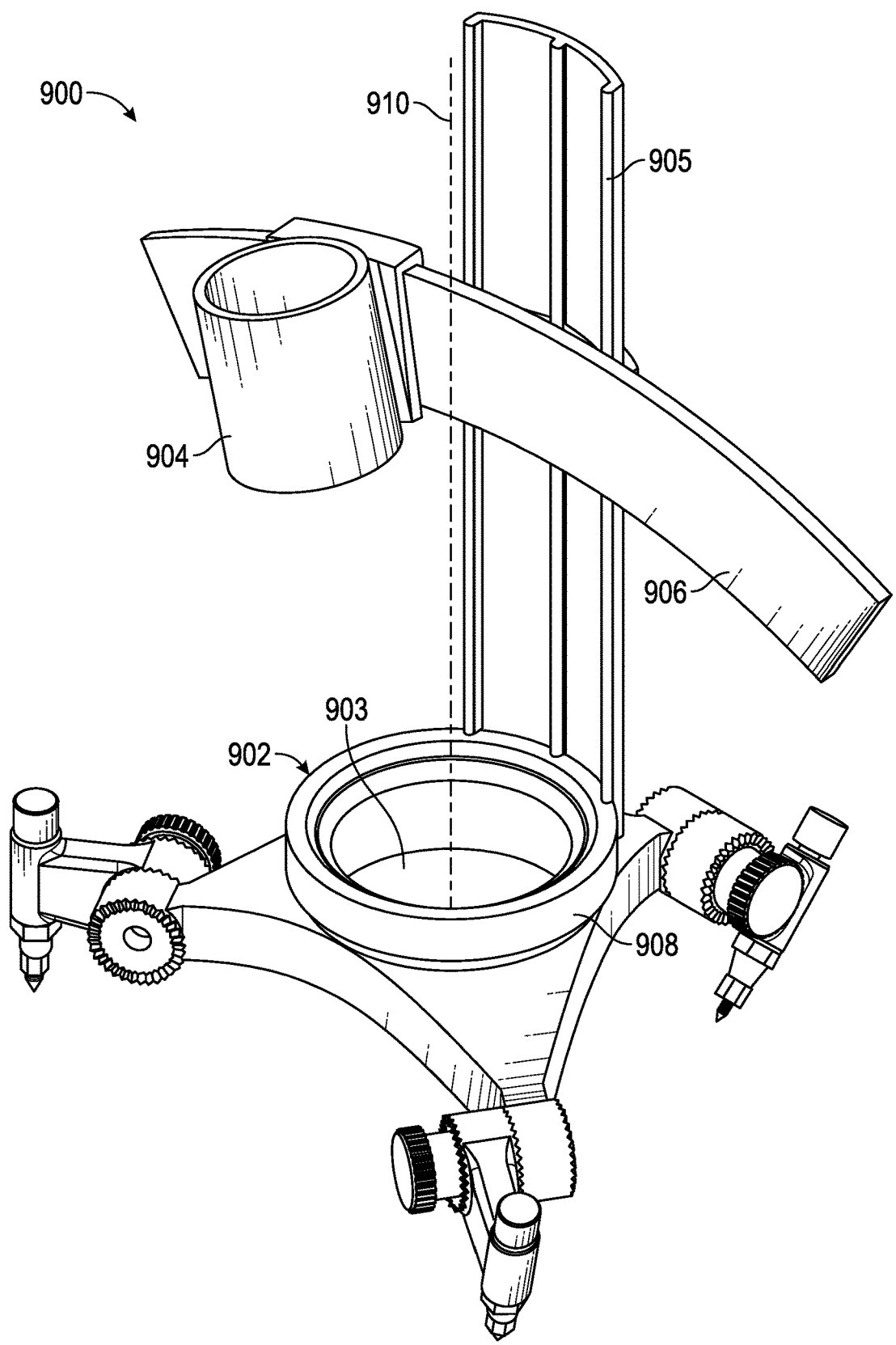
FIG. 9 shows an example of a "target-centered" skull mounted trajectory guide in which the base can be raised above the skull, such as described herein, such as described with respect to FIG. 8.

FIG. 9 shows an example of a "target-centered" skull mounted trajectory guide 900 in which the base 902 can be raised above the skull, such as described herein, such as with respect to FIG. 8. In an example, the base 902 need not include a ball and socket to establish the trajectory, but instead can include a sufficiently large opening providing a portal 903 through the base 902 and a movable aiming barrel 904. The aiming barrel 904 can include a contrast-enhanced imageable fiducial marker and can be movable along an arc 906. The arc 906 can be raised above the base 902 such as by one or more posts 905, such as can extend from a swivel 908 coupling the one or more posts 905 to the base 902 such as to allow 360 degree swiveling rotation about an axis 910 defined longitudinally through a center of the portal 903 in the base 902. The swivel can include respectively engaging rings, such as can also include bearings, if desired. Such swiveling can move the aiming barrel 904 to alter an approach direction of a trajectory provided by the aiming barrel 904. Moving the aiming barrel 904 along the arc 906 can vary the angle of the trajectory through the opening 903 and toward a common target location within the skull beyond a burr hole in the skull. The one or more posts 905 can include a guide slot or track. The guide slot or track can allow a vertical ("Z" direction) height location of the arc 906 to be adjusted upward or downward by the user. One or more thumbscrews or other securing devices can be used by the user to secure the arc to the one or more posts 905 such as adjustably at the desired height above the base 902. A lower "Z" height setting can correspond to a deeper target location beyond the skull. A higher "Z" height setting can correspond to a shallower target location beyond the skull. The arc 906 can be made rotatable around a center axis through the opening 903 in the base 902. This can include coupling the one or more posts 905 to the base 902 via a rotation ring that can engage the base 902 and can rotate about the base 902 and be secured in a desired rotational orientation, such as by a thumbscrew or other securing apparatus.

Figure 10:
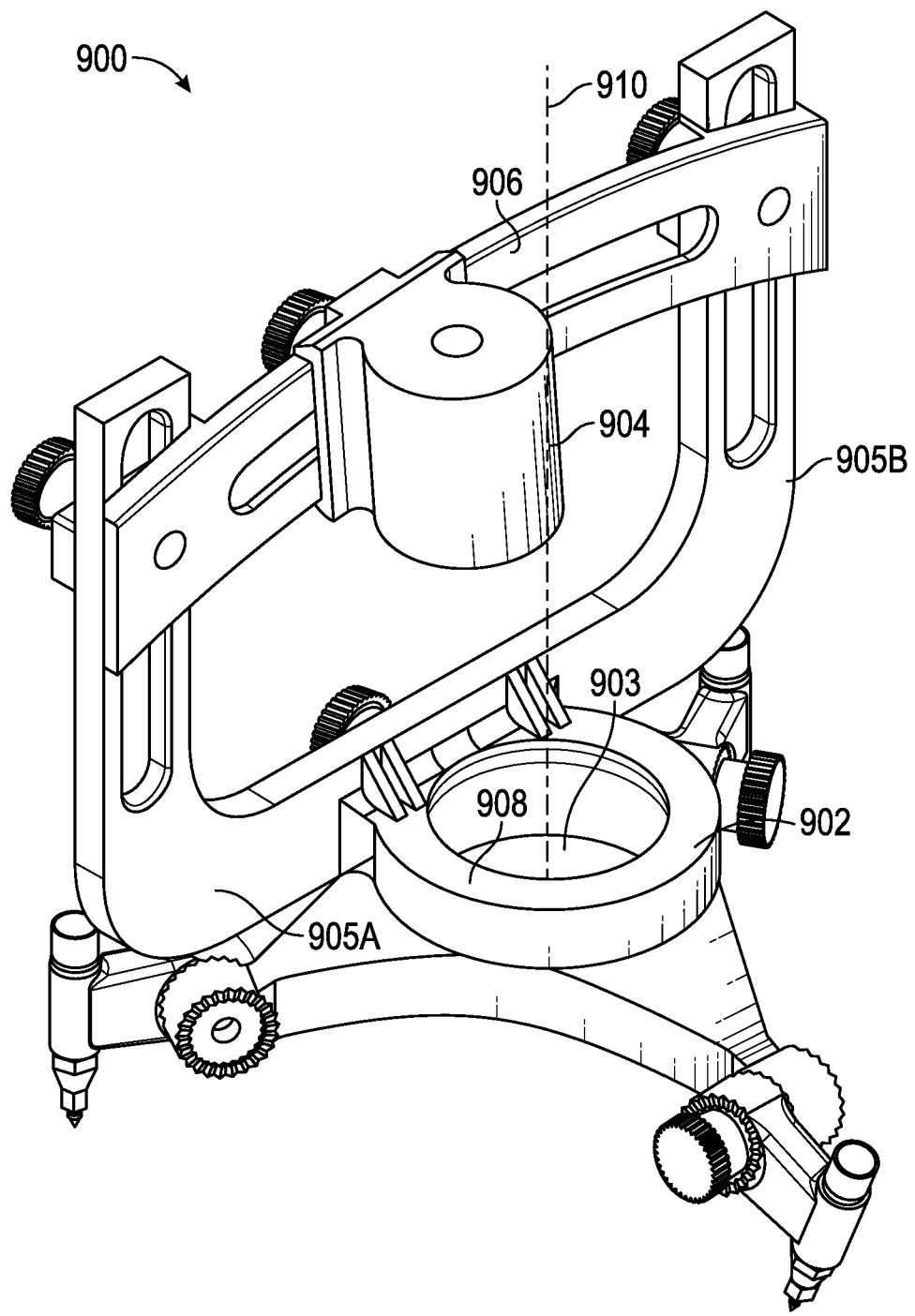
FIG. 10 shows an example of a "target-centered" skull mounted trajectory guide, such as described herein such as with respect to FIG. 9, but in which the arc can extend between two posts, such as to provide additional mounting stability for the arc.

FIG. 10 shows an example of a "target-centered" skull mounted trajectory guide 900, such as described herein such as above with respect to FIG. 9, but in which the arc 906 can extend between two posts 905A-B, such as to provide additional mounting stability for the arc 906.

The target centered trajectory guide alignment method can use initial alignment and placement using the fluid filled MRI/CT mechanism described herein, an image guided surgery system, such as the Medtronic Stealth® or Treon®, or a stereotactic head frame. The "Z" or "depth to target" can be the same for all procedures and can be set at initial alignment. One potential advantage of a target centered apparatus and method is that the entry point can be shifted such as to avoid one or more cortical vessels without changing the location of the target. One or more of the movable components (e.g., the barrel 904, the arc 906, the ball 110, the swivel 908, the retainer ring 810, guide stem 104, pivot sweep guide arch ring 126, threaded thumb wheel 402, etc.) can be robotically driven, such as by using a microactuator controlled by a microcontroller circuit or the like.

In an example, a method of establishing a trajectory using a target-centered embodiment, such as described herein such as with respect to FIGS. 9 and 10, can include: (1) mounting the base 902 to the subject's skull, such as about a burr hole in the skull; (2) performing imaging, such as by using an imageable fiducial marker such as described herein; (3) establishing the desired Z height, such as by adjusting the height of the arc 906 to give a desired distance to the target; and (4) rotating the arc 906 about a center axis extending vertically through the center of the opening 903, and/or sweeping the trajectory angle, such as by moving the barrel 904 along the arc 906, such as to determine a desired entry point, such as while maintaining a trajectory toward a desired fixed target location within the skull.

Although FIG. 8 showed an example of a raised base in combination with a ball-and-socket trajectory guide configuration, and FIGS. 9 and 10 showed examples of a raised base in combination with a "target centered" (e.g., arc and barrel) trajectory guide configuration, the raised base can also be used to provide a combined configuration, such as in which can provide a ball-and-socket trajectory guide and a target-centered trajectory guide. This can include a providing a base with a user-attachable and user-detachable ball-and-socket. When the user removes the ball-and-socket, such component removal can provide the opening 903 for a target-centered trajectory guide, other user-attachable and detachable components of which (e.g., the one or more posts 905, the barrel 904, etc.) can then be attached by the user.

Figure 11:
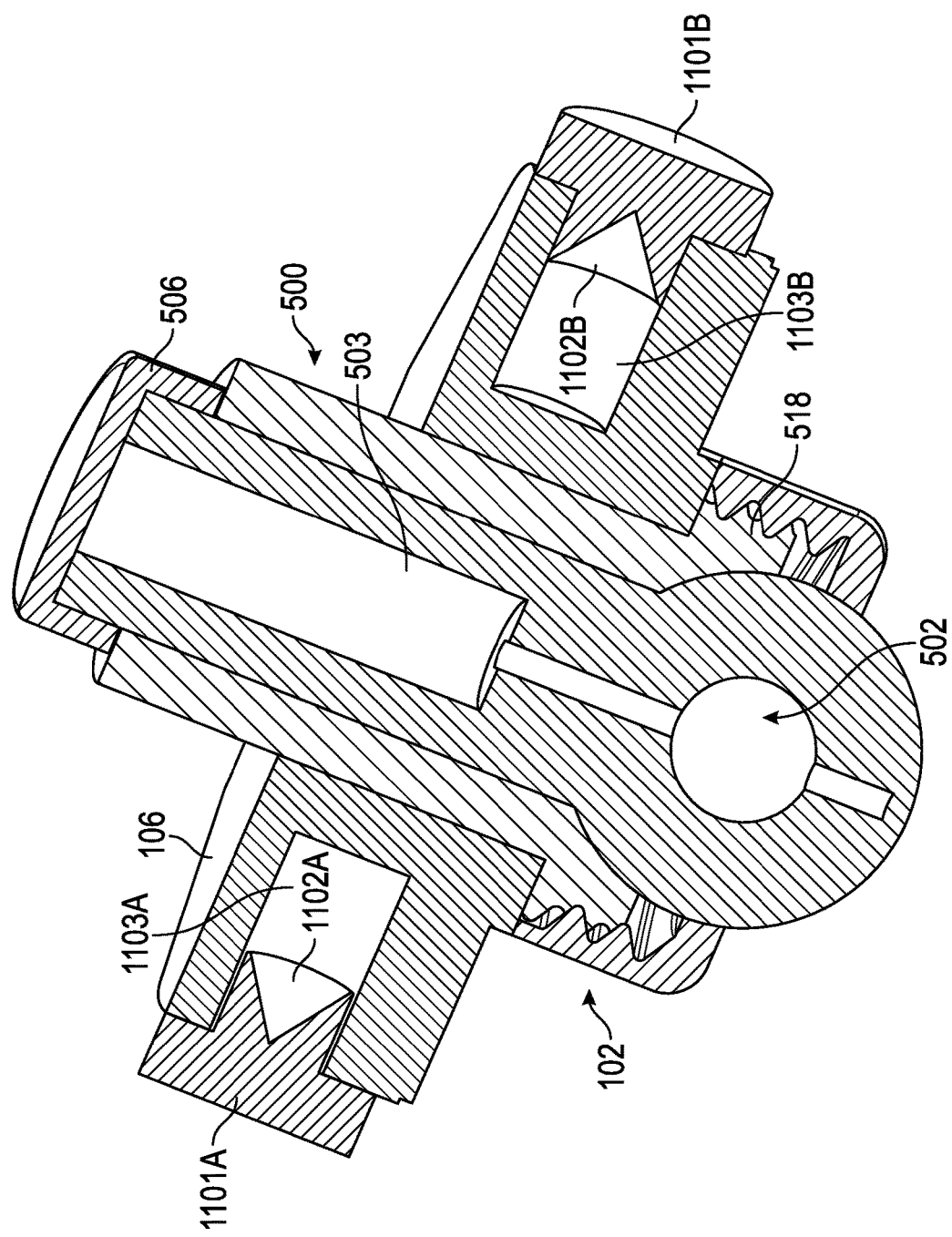
FIG. 11 shows an example, similar to that shown and described above with respect to FIG. 5A, but in which a trajectory guide can include certain components having imageable fiducial markers.

FIG. 11 shows an example in which the trajectory guide 100 can include certain components having imageable fiducial markers, similar to that shown and described above with respect to FIG. 5A. In the example of FIG. 11, the flange 106 can include MR, CT, or other imageable fiducial markers 1101A-B, such can be located on opposing lateral edges of the flange 106. The fiducial markers 1101A-B can be sized, shaped, or otherwise configured to fit into corresponding or mating receptacles 1103A-B on the opposing lateral sides of the flange 106. The user can visually align (e.g., with or without using imaging information) such fiducial markers 1101A-B in an anterior-posterior (A-P) or other desired direction, which can then be verified or compensated for during pre-operative or intraoperative imaging. The fiducial markers 1101A-B can be fluid-filled with a contrast agent. The fiducial markers 1101A-B can include recessed portions or can otherwise be shaped or configured so as to respectively provide "arrows" 1102A-B or another imageably visualizable indication of directionality. In the example of FIG. 11, in addition to being able to provide a fluid volume 502 that indicates the pivot point, the fiducial markers 1101A-B can provide imageable volumes on opposing lateral portions of the trajectory guide flange 106 that allow indication of anterior and posterior directions to appear in a distinguishable manner on images provided by the imaging modality. This can allow workstation software to compensate for any possible misalignment of the actual placement of the trajectory guide with respect to the actual anterior and posterior directions, such as can be determined using software processing of images obtained using the imaging modality.

Figure 12A:
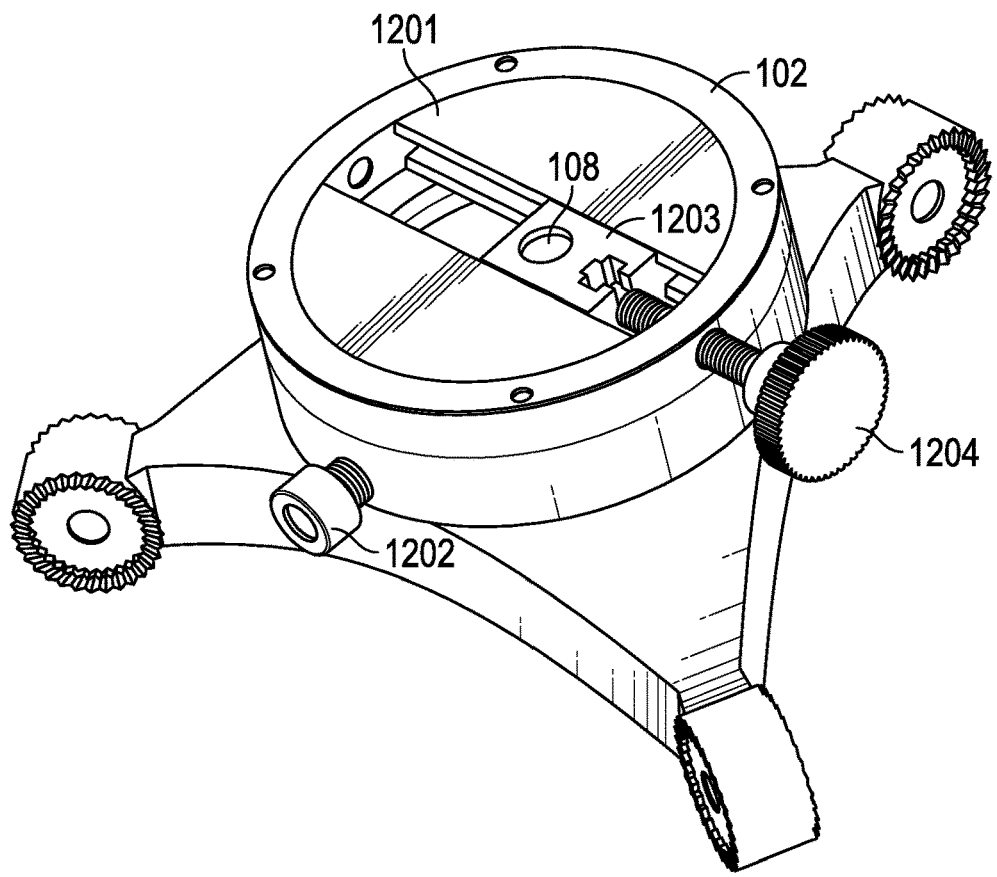
FIGS. 12A-B shows an example, similar to that shown and described with respect to FIG. 8, in which the trajectory guide can include a base that can include an adjustable stage, such as for polar-offset or x-y adjustment.
Figure 12B:
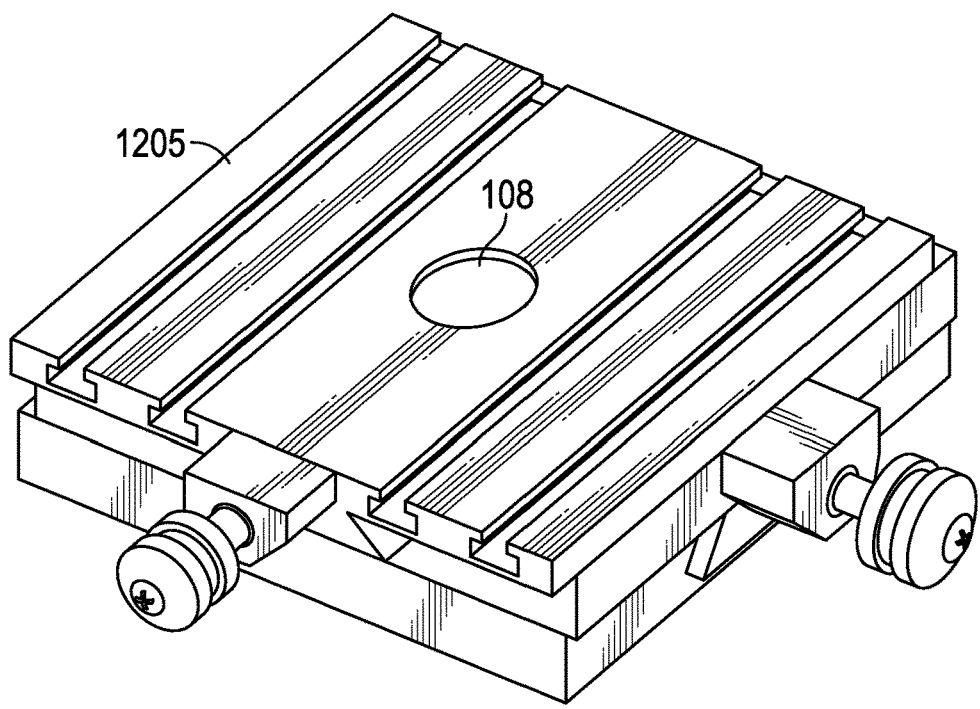
Figure 13A:
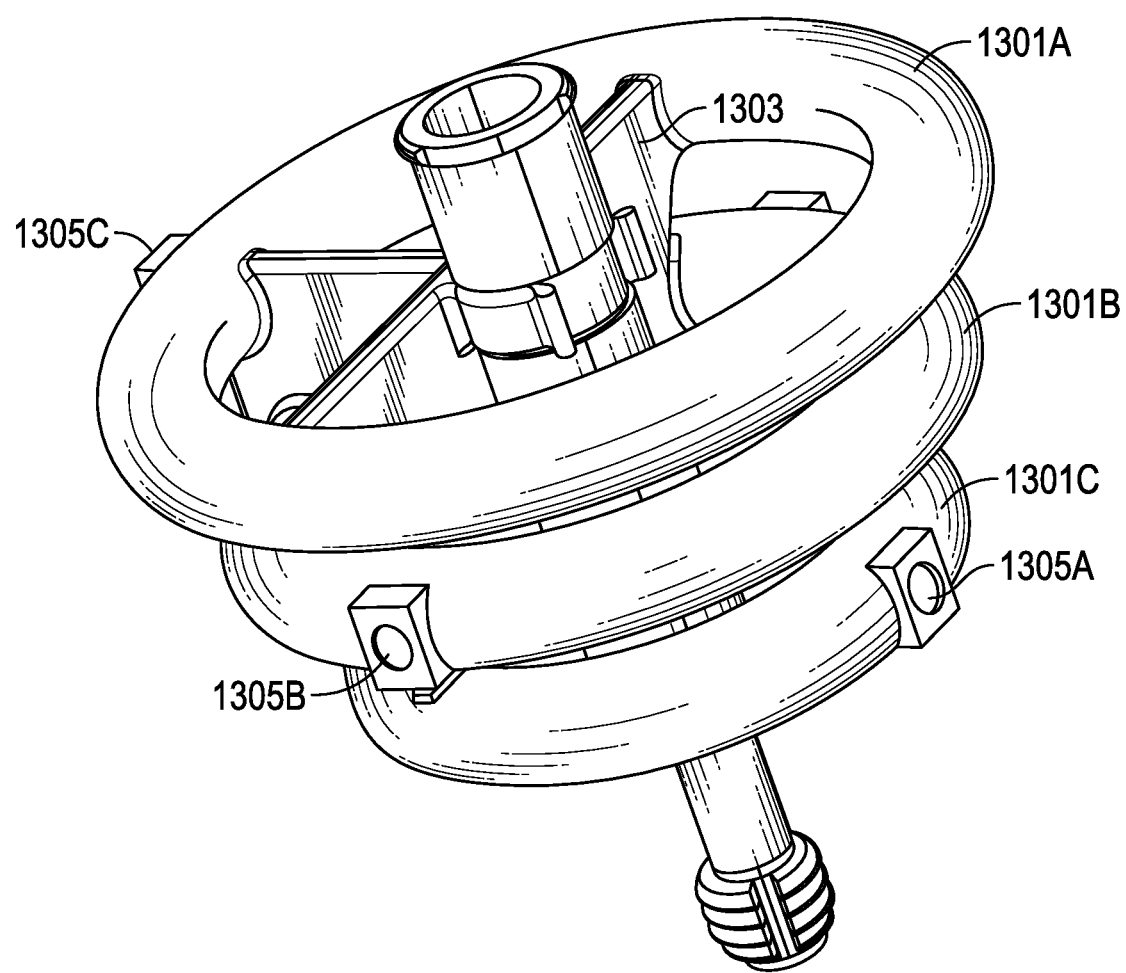
Figure 13B:
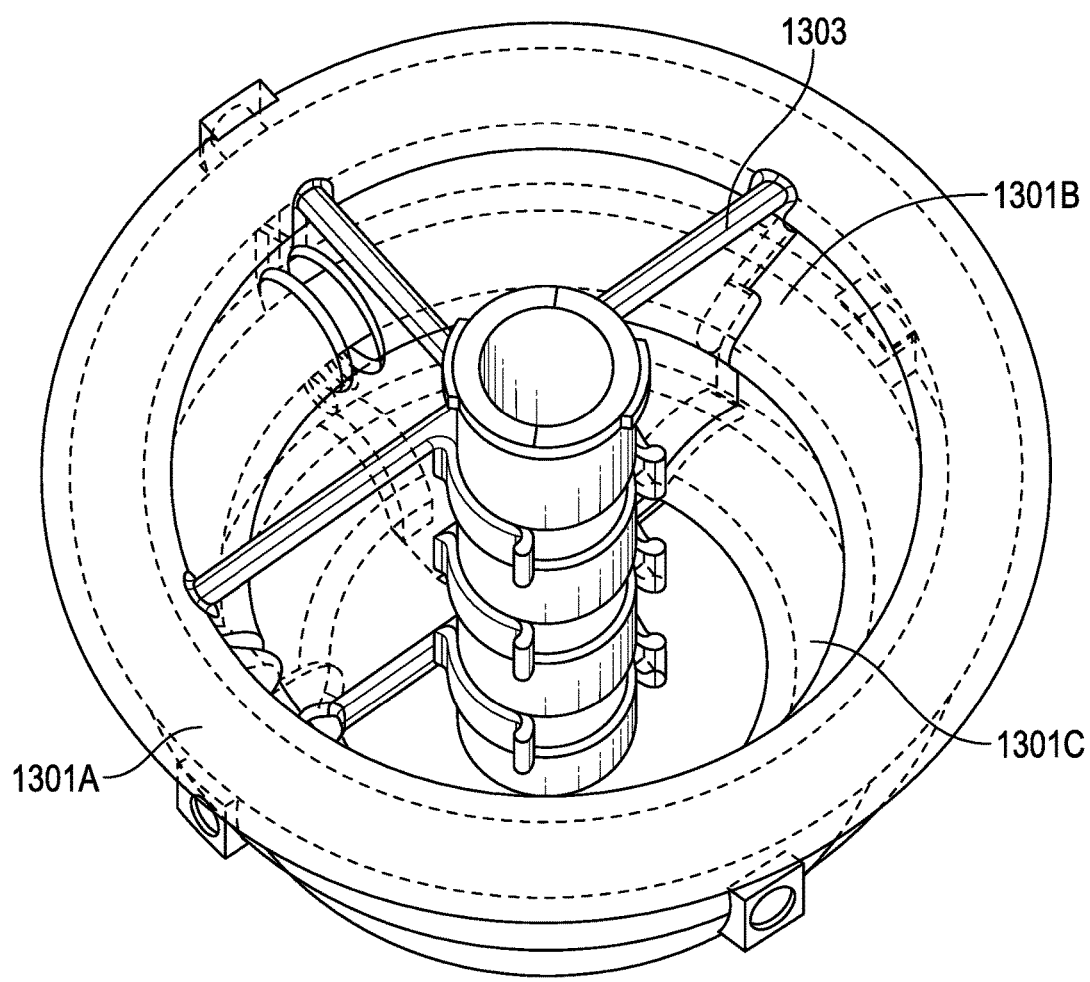

FIGS. 12A-B shows an example, similar to that shown and described with respect to FIG. 8, in which the trajectory guide 100 can include a base 102 that can include an adjustable stage 1201. The adjustable stage 1201 can allow the user or controller device to adjust a location of the socket 108 (and the ball 110 carried therein), such as within an adjustment plane. In an example, the stage 1201 can provide angle polar offset, such as by using a circular disk stage 1201 that can rotate within the base 102, such as a full 360 degrees about a longitudinal center axis defined by a correspondingly sized circular receptacle of the base 102 that receives the circular disk stage 1201. The circular disk stage 1201 can be secured in a desired angular orientation, such as by a thumbscrew 1202. The circular disk stage 1201 can also include a lateral (side-to-side) translatable sub-stage 1203, such as can allow the socket 108 (and the ball 110 carried therein) to be laterally translated and repositioned by a user or by a controller device, such as by manipulating a thumbscrew 1204 engaging both the base 102 and the sub-stage 1203. FIG. 12B shows an example of an x-y stage 1205, which can similarly be placed within a corresponding receptacle in the base 102, such as to allow translation of the socket 108 back-and-forth in an x-direction and also back-and-forth in a y-direction. Either of the adjustable stages 1201 or 1205 can be used with the base 102 without the socket 108 and ball 110, if desired. In such a case, socket 108 as shown in FIGS. 12A-B can be replaced by an appropriately-sized lumen to guide therethrough a correspondingly sized instrument, such as a catheter, a recording or stimulation electrode, or the like. For example, in a microelectrode recording application (e.g., for epilepsy diagnosis or characterization), a polar-offset or x-y adjustable stage for a trajectory guidance lumen (without requiring a socket 108 and ball 110) can be useful such as for mapping an x-y grid of locations on a surface of the brain, such as along parallel but laterally offset trajectories.

FIGS. 13A, 13B, 13C, 13D, and 13E show an example of two or more concentric ring imageable fiducial marker rings 1301A-C, such as can be clipped or snapped onto or otherwise affixed to a proximal portion of the guide stem 104, such as using a clip-on rack 1303 that can include multiple clips that clip onto respective recessed portions of the guide stem 104. The rack 1303 can arrange the locations of the rings 1301A-C with respect to each other. The rings 1301A-C can be affixed to the rack 1303 in concentric alignment with each other. The rings 1301A-C can be in a tapered arrangement such that they are progressively smaller in diameter. For example, the ring 1301C can be smaller in diameter than the ring 1301B, which, in turn, can be smaller in diameter than the ring 1301A. The outer diameter of a smaller ring can be smaller than an inner diameter of the next larger ring such that, when directly viewed concentrically looking from a proximal end of the guide stem 104 toward a distal end of the guide stem 104, a small gap between the rings can be seen.

The rings 1301A-C can be fluid-filled, e.g., with an imageable contrast agent to enhance their visibility on a desired imaging modality, such as via fluid-fill ports 1305A-C. The fluid fill ports 1305 can be located at desired locations about the circumference of the set of rings 1301, such as at 0 degrees, 90 degrees, and 180 degrees, as shown in FIG. 13D. The fluid fill ports 1305 can include an additional volume of the contrast agent such that the fluid fill ports 1305 themselves can be visible on an imaging modality, and the orientation of the fluid fill ports 1305 can thereby be used as fiducial marker indicators. The rings 1301 can be progressively smaller in diameter to visually show on an image produced by an imaging modality the "TARGET CENTERED" when aligned in an orthogonal view of the trajectory. The rings 1301 and rack 1303 can be rotated together such that the fluid fill ports 1305 (visible on the image by their contrast agent fluid) can provide reference for anterior-posterior and medial-lateral directions.

Figure 14:
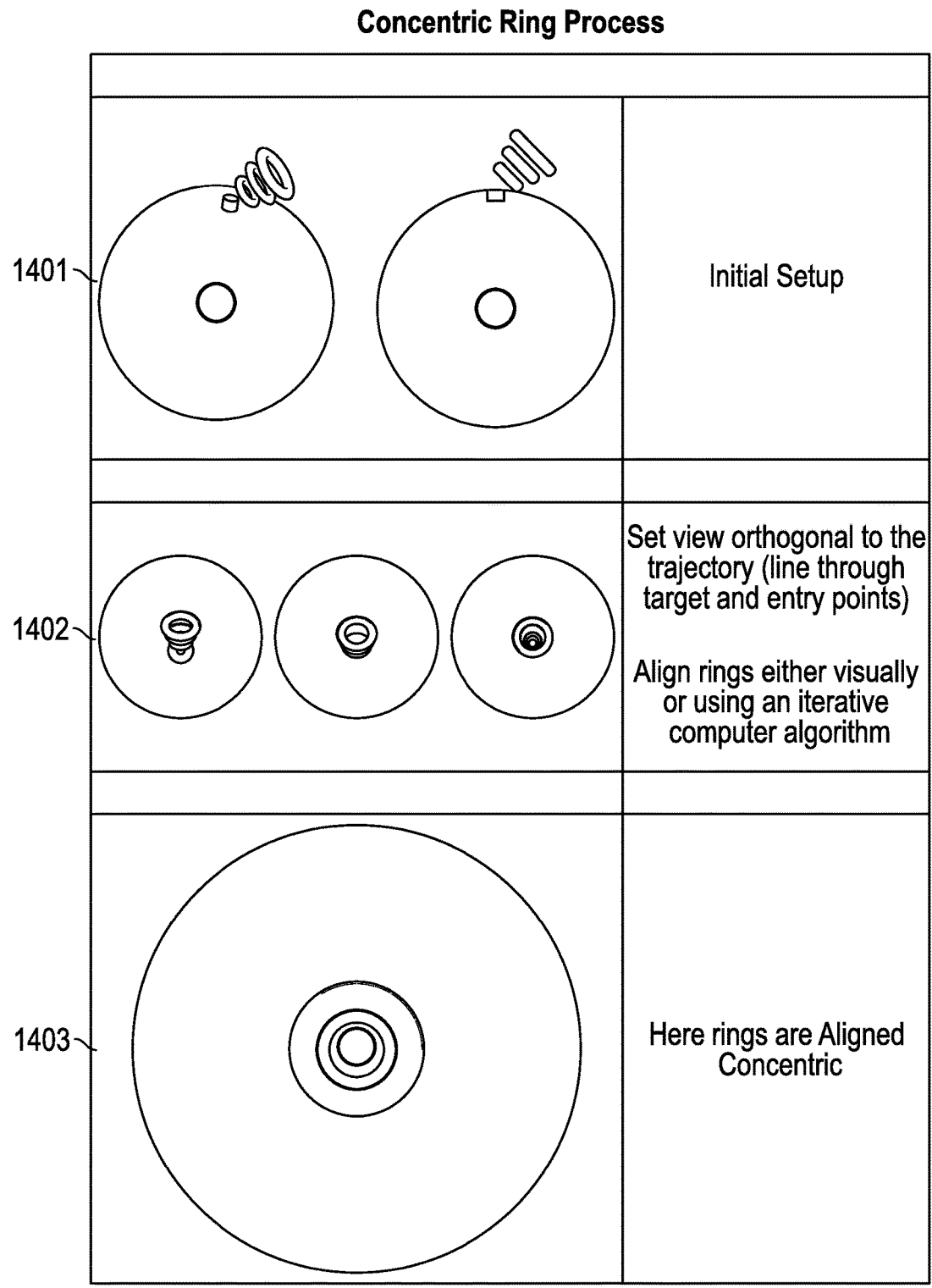
FIG. 14 is a diagram illustrating an example of trajectory guide alignment using a tapered arrangement of concentric rings.

FIG. 14 is a diagram illustrating an example of trajectory guide alignment using the tapered arrangement of concentric rings 1301A-C. At 1401, an example of an arrangement of the rings 1301 during initial setup is shown, together with the entry point, the target, and the trajectory. At 1402, a view on the imaging modality is set orthogonal to the trajectory (line through the target and entry points). The guide stem 104 is then adjusted (manually or using a controller device) until the rings are concentrically aligned, as shown at 1403, such as with the gaps between the progressively smaller rings visible to indicate alignment.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permuta- The claimed invention is:

1. A medical instrument trajectory guide comprising:
a base, including a socket;
a ball, sized and shaped to be located in the socket, the ball including a lumen therethrough;
a guide stem, sized and shaped to be attached to the ball, the guide stem including a lumen aligning with the lumen of the ball when the guide stem is attached to the ball; and
a plurality of contrast-enhanced imageable fiducial marker rings arranged concentrically about the guide stem, wherein the rings are progressively smaller in diameter in a longitudinal direction of the guide stem.

2. The trajectory guide of claim 1, wherein the arch includes a coupling that is sized and shaped to engage the base such that the arch is rotatable with respect to the base.

3. The trajectory guide of claim 1, wherein the guide stem includes:
a first guide stem portion, including a first lumen;
a second guide stem portion, including a second lumen that is coaxially aligned with the first lumen of the first guide stem portion; and
wherein the first and second guide stem portions are adjustably engaged to each other to allow longitudinal adjustment of the first and second guide stem portions to define a height of the guide stem given by a combined length of the first and second guide stem portions.

4. The trajectory guide of claim 1, further comprising an imaging stem, sized and shaped to replicate the guide stem and the ball in engagement, the imaging stem including a machine-imagable fiducial marker including a contrast agent indicating a pivot point of the ball.

5. The trajectory guide of claim 4, wherein the imaging stem further includes a machine-imageable fiducial marker including a contrast agent indicating a longitudinal axis of the guide stem.

6. The trajectory guide of claim 1, wherein the base includes a plurality of legs extending distally therefrom, the legs sized and shaped to raise the base above an entry point on a subject's skull.

7. The trajectory guide of claim 1, further comprising contrast-enhanced machine-imageable fiducial markers located on opposing lateral portions of the base to indicate an alignment of the base with an anterior-posterior direction on an image of the base seated on a subject's skull.

8. The trajectory guide of claim 7, wherein the adjustable stage provides an x-y translational adjustment of the socket.

9. The trajectory guide of claim 1, further comprising an adjustable stage, located at or engaged to the base, to allow in-plane adjustment of a location of the socket within the base.

10. The trajectory guide of claim 9, wherein the adjustable stage provides a polar angle adjustment of the socket and a lateral translational adjustment of the socket.

11. The trajectory guide of claim 1, wherein the rings are arranged such that there is a gap visible between the rings on an image when viewed directly longitudinally from an end of the guide stem.

12. A medical instrument trajectory guide comprising:
a base, including:
a socket;
a plurality of legs extending distally therefrom, the legs sized and shaped to raise the base above an entry point on a subject's skull; and
an adjustable stage, located at or engaged to the base, to allow in-plane adjustment of a location of the socket within the base;
a ball, sized and shaped to be located in the socket, the ball including a lumen therethrough;
a guide stem, sized and shaped to be attached to the ball, the guide stem including a lumen aligning with the lumen of the ball when the guide stem is attached to the ball, wherein the guide stem includes:
a first guide stem portion, including a first lumen;
a second guide stem portion, including a second lumen that is coaxially aligned with the first lumen of the first guide stem portion; and
wherein the first and second guide stem portions are adjustably engaged to each other to allow longitudinal adjustment of the first and second guide stem portions to define a height of the guide stem given by a combined length of the first and second guide stem portions;
an arch, coupled to the socket, the arch extending upward over the ball, the arch sized and shaped to be coupled to the ball-attached guide stem to constrain movement of the guide stem in a specified relationship to the arch, wherein the arch includes a coupling that is sized and shaped to engage the base such that the arch is rotatable with respect to the base; and
a plurality of contrast-enhanced imageable fiducial marker rings arranged concentrically about the guide stem such that the rings are progressively smaller in diameter in a longitudinal direction of the guide stem, such that there is a gap visible between the rings on an image when viewed directly longitudinally from an end of the guide stem.

13. A ball-and-socket-free medical instrument trajectory guide comprising:
a base, including a portal;
a height-adjustable arc, coupled to the base, the arc extending upward over the base, the arch located at an adjustable vertical distance in a proximal direction from the base;
a swivel, rotatably coupling the arc to the base to permit rotation about a longitudinal axis defined by the portal in the base;
a movable ball-and-socket-free aiming barrel, including a lumen therethrough and slidably engaged to the arc, such that after adjusting a vertical distance of the arc in a proximal direction from the base, either (1) swiveling the arc, or (2) moving the aiming barrel along the arc, varies a direction of a trajectory through the portal and toward a specified target location beyond a burr hole in a skull.

14. The trajectory guide of claim 13, wherein the arc is adjustably suspended between a pair of posts extending proximally from the base.

15. The trajectory guide of claim 13, comprising a plurality of legs, extending distally from the base, the legs sized and shaped to raise the base above an entry point on a subject's skull.

16. A ball-and-socket-free medical instrument trajectory guide for providing target-centered alignment of a trajectory to deliver an instrument along the trajectory toward a desired target location beyond an entry portal, in a subject, about which a trajectory guide base has been mounted, the trajectory guide comprising:
means for adjusting a Z-height of a trajectory guide lumen such that a trajectory provided by the lumen will still intersect the desired target location beyond an entry portal in the subject after further adjusting an approach angle or approach direction of the trajectory; and ball-and-socket-free means for adjusting at least one of:

the approach angle of the trajectory along a constrained arc; and an approach direction of the trajectory by rotatably swiveling the trajectory guide lumen with respect to the base.

17. The trajectory guide of claim 16, wherein the means for adjusting at least one of the the approach angle of the trajectory or adjusting the approach direction of the trajectory includes:

fiducial marker means for visualizing, in an image produced using an imaging modality, contrast-imageable fiducial marker concentric rings along a desired path to the desired target location and adjusting at least one of the approach angle of the trajectory or the approach direction of the trajectory until the concentric rings are concentrically aligned in the image.

18. The trajectory guide of claim 17, wherein the concentric rings are progressively smaller in a longitudinal direction of the trajectory.

19. The trajectory guide of claim 16, wherein the means for adjusting the Z-height, adjusting the approach angle, and adjusting the approach direction include means for performing robotically using a control circuit and actuators.

* * * * *